(12) United States Patent
Lock et al.

(10) Patent No.: US 11,890,300 B2
(45) Date of Patent: Feb. 6, 2024

(54) IMMUNE CELLS EXPRESSING AN ANTIGEN BINDING RECEPTOR AND A CHIMERIC COSTIMULATORY RECEPTOR

(71) Applicant: Miltenyi Biotec GmbH, Bergisch Gladbach (DE)

(72) Inventors: Dominik Lock, Cologne (DE); Mario Assenmacher, Bergisch Gladbach (DE); Andrew Kaiser, Rosrath (DE)

(73) Assignee: Miltenyi Biotec B.V. & Co. KG, Bergisch Gladbach (DE)

( * ) Notice: Subject to any disclaimer, the term of this patent is extended or adjusted under 35 U.S.C. 154(b) by 1167 days.

(21) Appl. No.: 16/465,750

(22) PCT Filed: Dec. 11, 2017

(86) PCT No.: PCT/EP2017/082127
§ 371 (c)(1),
(2) Date: May 31, 2019

(87) PCT Pub. No.: WO2018/108766
PCT Pub. Date: Jun. 21, 2018

(65) Prior Publication Data
US 2019/0388468 A1 Dec. 26, 2019

(30) Foreign Application Priority Data
Dec. 15, 2016 (EP) ..................................... 16204414

(51) Int. Cl.
*A61K 35/15* (2015.01)
*C07K 14/705* (2006.01)
*C07K 14/725* (2006.01)
*A61K 35/17* (2015.01)
*C07K 16/28* (2006.01)
*C07K 16/30* (2006.01)
*C12N 5/0783* (2010.01)

(52) U.S. Cl.
CPC .......... *A61K 35/15* (2013.01); *C07K 14/7051* (2013.01); *C07K 14/70507* (2013.01); *C07K 14/70517* (2013.01); *C07K 14/70521* (2013.01); *C07K 16/2887* (2013.01); *C07K 16/3053* (2013.01); *C12N 5/0638* (2013.01); *A61K 35/17* (2013.01); *C07K 2317/31* (2013.01); *C07K 2317/622* (2013.01); *C07K 2319/03* (2013.01); *C07K 2319/33* (2013.01); *C12N 2510/00* (2013.01); *C12N 2740/16043* (2013.01)

(58) Field of Classification Search
CPC ............ C07K 14/7051; C07K 2319/03; C07K 2319/33; A61K 35/17
See application file for complete search history.

(56) References Cited

U.S. PATENT DOCUMENTS

| | | | |
|---|---|---|---|
| 10,703,794 B2 * | 7/2020 | Maher | C07K 14/705 |
| 2014/0099309 A1 | 4/2014 | Powell et al. | |
| 2015/0342993 A1 * | 12/2015 | Kloss | A61K 39/001114 435/325 |
| 2019/0315879 A1 * | 10/2019 | Kaiser | C07K 16/18 |

FOREIGN PATENT DOCUMENTS

| | | | | |
|---|---|---|---|---|
| EP | 3315511 | | 5/2018 | |
| JP | 2015092865 | | 5/2015 | |
| WO | WO-2012082841 A2 * | | 6/2012 | ............ A61K 35/17 |
| WO | WO 2013044225 | | 3/2013 | |
| WO | WO 2014100615 | | 6/2014 | |
| WO | WO 2015057852 | | 4/2015 | |
| WO | WO 2016123122 | | 8/2016 | |
| WO | WO 2016154621 | | 9/2016 | |
| WO | WO 2016168769 | | 10/2016 | |
| WO | WO 2016168773 | | 10/2016 | |
| WO | WO-2018078066 A1 * | | 5/2018 | ......... A61K 31/4188 |

OTHER PUBLICATIONS

Fesnak et al., Nature Reviews Cancer, 16:566-581 (Year: 2016).*
Dai et al., "Chimeric antigen receptors modified T-cells for cancer therapy," Journal of the National Cancer Institute, Jul. 1, 2016, 108(7):div439, 14 pages.
European Search Report in European Application No. 16204414.3, dated Feb. 15, 2017, 7 pages.
International Preliminary Report on Patentability in International Application No. PCT/EP2017/082127, dated Jun. 18, 2018, 7 pages.
Roybal et al., "Precision tumor recognition by T cells with combinatorial antigen-sensing circuits," Cell, Feb. 11, 2016, 164(4):770-9.
Wu et al., "Remote control of therapeutic T cells through a small molecule-gated chimeric receptor," Science, Oct. 16, 2015, 350(6258):aab4077, 11 pages.
International Search Report and Written Opinion in PCT Appln. No. PCT/EP2017/082127, dated Feb. 23, 2018, 10 pages.
Extended Search Report in European Appln. No. 16196487.9, dated Mar. 20, 2017, 7 pages.
Grote et al., "Adapter chimeric antigen receptor (AdCAR)-engineered NK-92 cells: An off-the-shelf cellular therapeutic for universal tumor targeting," Oncoimmunology, Jan. 1, 2020, 9(1):1825177, 11 pages.
International Preliminary Report on Patentability in International Appln. No. PCT/EP2017/077545, dated May 9, 2019, 8 pages.
International Search Report and Written Opinion in PCT Appln. No. PCT/EP2017/077545, dated Jan. 1, 2018, 10 pages.
Seitz et al., "Novel adapter CAR-T cell technology for precisely controllable multiplex cancer targeting," Oncoimmunology, Jan. 1, 2021, 10(1):2003532, 16 pages.

* cited by examiner

*Primary Examiner* — Jessica H Roark
(74) *Attorney, Agent, or Firm* — Christian Biervert; Fish & Richardson P.C.

(57) ABSTRACT

The present invention provides an immune effector cell that comprises a chimeric antigen receptor (CAR) specific for a tag of a tagged polypeptide, wherein said polypeptide binds to an antigen of a target cell, and a chimeric costimulatory receptor (CCR) specific for a further antigen. The CCR is not able to mediate said immune response on its own but boosts the immune response of said immune effector cell triggered by the CAR.

10 Claims, 14 Drawing Sheets

Specification includes a Sequence Listing.

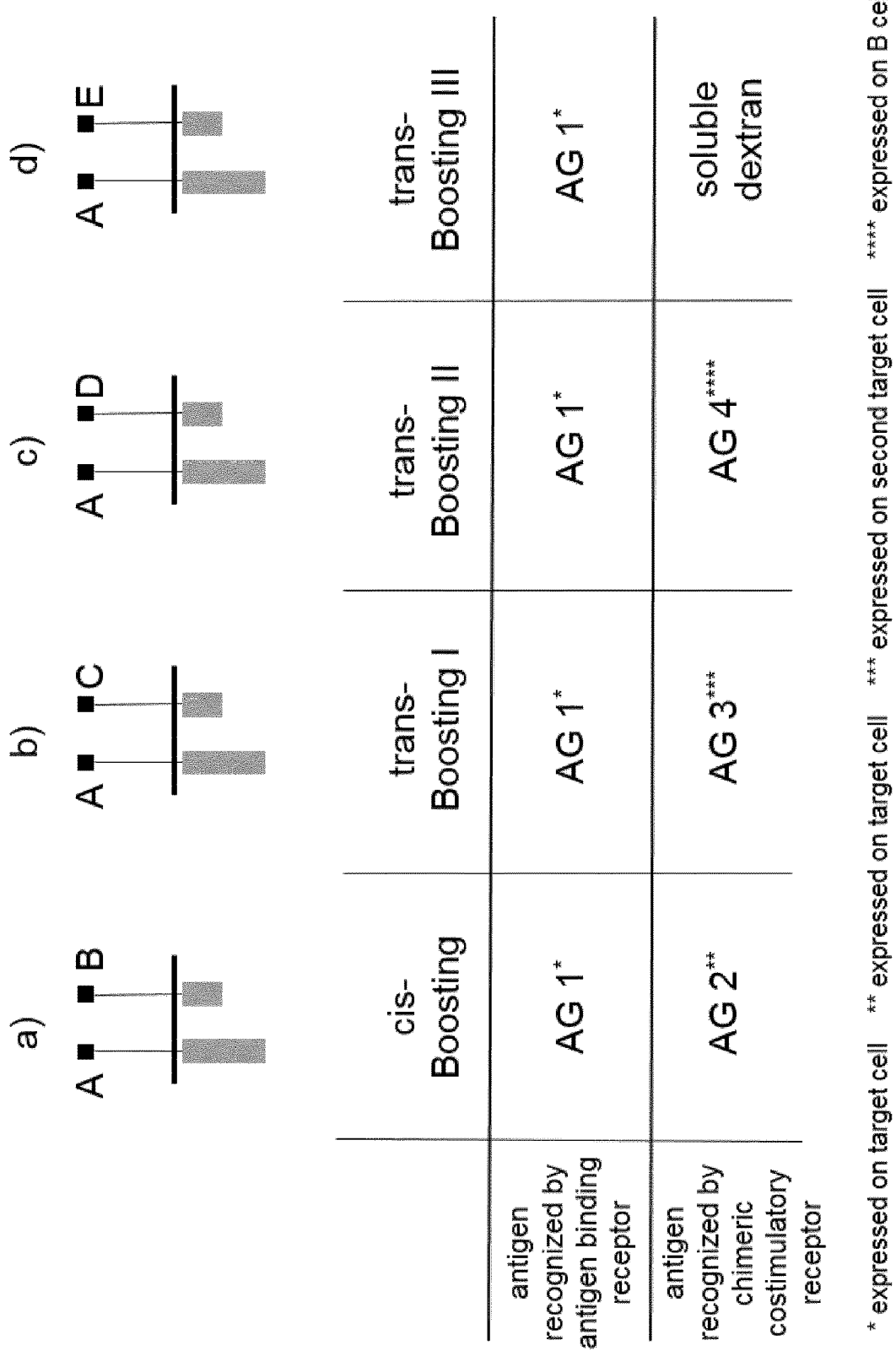
FIG 1a-d

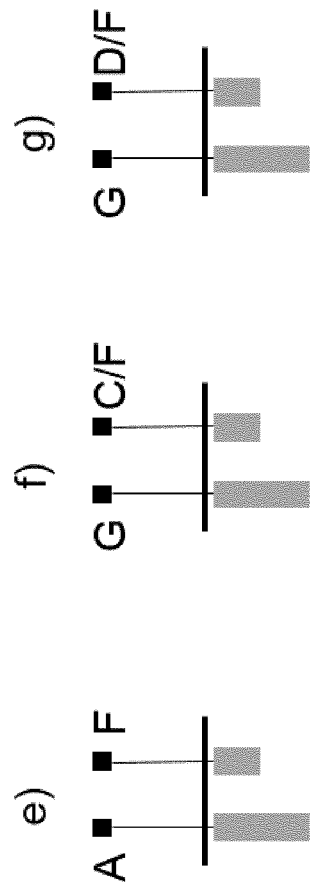
FIG 1e-g

IMMUNE CELLS EXPRESSING AN ANTIGEN BINDING RECEPTOR AND A CHIMERIC COSTIMULATORY RECEPTOR

FIELD OF THE INVENTION

The present invention generally relates to the field of antigen binding receptors, e.g. chimeric antigen binding receptors (CARs) expressed on the surface of immune cells for treatment of a disorder such as cancer, in particular to immune cells that co-express a chimeric costimulatory receptor (CCR).

BACKGROUND OF THE INVENTION

The redirection of T cells to tumor antigens by expressing transgenic chimeric antigen receptors takes advantage of potent cellular effector mechanisms via human leukocyte antigen (HLA)—independent recognition. The potential of this approach has recently been demonstrated in clinical trials, wherein T cells expressing CAR were infused into adult and pediatric patients with B-cell malignancies, neuroblastoma, and sarcoma. CARs are recombinant receptors that typically target cell surface molecules. CARs are typically composed of an extracellular antigen-recognition moiety that is linked, via spacer/hinge and transmembrane domains, to an intracellular signaling domain that can include costimulatory domains and T cell activation moieties. CARs recognize unprocessed antigens independently of their expression of major histocompatibility antigens, which is unlike the physiologic T cell receptors (TCRs). Hence, CAR T cells can circumvent some of the major mechanisms by which tumors avoid major histocompatibility class (MHC)—restricted T cell recognition such as the downregulation of HLA expression or proteasomal antigen processing, two mechanisms that contribute to tumor escape from TCR-mediated immunity. Another feature of CARs is their ability to bind not only to proteins but also to carbohydrate, ganglioside, proteoglycan, and heavily glycosylated protein, thereby expanding the range of potential targets. CARs engage the target via the antigen recognition moiety, often a single-chain variable fragment (scFv) derived from antibodies or a Fab fragment (reviewed e.g. in Dai et al., 2016, *J Natl Cancer Inst* 108(7): djv439).

WO2014/055657A1 discloses a trans-signaling composition comprising a nucleic acid molecule comprising a sequence encoding a first CAR and a second CAR, wherein the first CAR comprises a first antigen binding domain, a first transmembrane domain, and an intracellular domain of a costimulatory molecule and wherein the second CAR comprises a second antigen binding domain, a second transmembrane domain, and an intracellular domain of a T cell receptor, regularly a sole CD3ζ signaling domain. The first antigen binding domain binds a first target and the second antigen binding domain binds a second target, wherein the first and second target are each a tumor antigen associated with a solid tumor. Sufficient CAR T cell activation occurs only when the intracellular domain of the T cell receptor from the first CAR is active and the intracellular domain of the co-stimulatory molecule from the second CAR is active in the T cell. It is a disadvantage of the disclosed CAR system that in a hostile and immunosuppressive solid tumor microenvironment the CAR T cell response is very difficult to instigate and sustain.

In WO2014/055668A1 an immune-responsive cell is disclosed the cell comprising a) an antigen recognizing receptor that binds a first antigen with low affinity, wherein binding of the receptor to the first antigen activates the immune-responsive cell, and b) a chimeric co-stimulating receptor (CCR) that binds a second antigen and stimulates the immune-responsive cell. The intracellular signaling domain of the antigen recognizing receptor consist solely of the CD3ζ signaling domain. The activation of an immune-responsive cell by binding of the antigen recognizing receptor to the first antigen leads to an induction of signal transduction or changes in protein expression in the cell resulting merely in initiation of an immune response. The stimulation of an immuno-responsive cell by the binding of the CCR to a second antigen leads to a signal that results in a robust and sustained immune response after immune cell activation which is not possible with the activation of the first receptor on its own. The antigens are selected from tumor antigens or virus antigens.

WO2015/07547A1 discloses a T cell which co-expresses a first chimeric antigen receptor (CAR) and second CAR at the cell surface, each CAR comprising, (i) an antigen binding domain, (ii) a spacer, (iii) a trans-membrane domain, and (iv) an endodomain wherein the antigen binding domains of the first and second CARs bind to different antigens, and wherein one of the first or second CARs is an activating CAR comprising an activating endodomain and the other CAR is an inhibitory CAR comprising a ligation-on inhibitory endodomain.

Roybal et al (2016, *Cell* 164, 1-10) engineered a combinatorially activated T cell circuit in which a synthetic Notch receptor for one antigen induces the expression of a CAR for a second antigen. These dual-receptor AND-gate T cells are only armed and activated in the presence of dual antigen tumor cells. These T cells show precise therapeutic discrimination in vivo sparing single antigen "bystander" tumors while efficiently clearing combinatorial antigen "disease" tumors.

Generally, tumor cells can secrete cytokines that recruit suppressive cells such as $T_{reg}$, immature dendritic cells or myeloid-derived suppressor cells that inhibit T cell responses through a variety of mechanisms e.g. release of immune suppressive cytokines like IL10 or TGFβ. This leads to a microenvironment where immune responses are difficult to instigate and sustain. Furthermore, due to tumor heterogeneity, tumor cells which are less immunogenic or have up-regulated immune suppressive factors are selected. These cells are able to subvert the immune response and escape immune surveillance.

Therefore, there is a need in the art for an improved or alternative receptor system, e.g. a CAR system, expressed on the surface of an immune cell that allow a treatment of a disorder such as cancer using said immune cell.

SUMMARY OF THE INVENTION

A gene modified cell co-expressing a target reactive receptor, i.e. an antigen binding receptor such as a CAR, and a boosting receptor, i.e. a chimeric costimulatory receptor (CCR), can e.g. diminish the effects of an inhospitable tumor environment, i.e. an immunosuppressive milieu which is often associated with a declined tumor reactivity of gene modified immune cells or can e.g. ensure survival of the gene modified immune cell. For example, gene-modified immune cells expressing a CAR down-regulate and/or inactivate their CAR in such inhospitable tumor environments and therefore are strongly restricted with regard to their cytolytic potential. These gene modified cells have also an improved persistence in a subject and may be re-boosted in the case of a potential tumor recurrence by re-activation of the boosting receptor. The target reactive receptor may be a first antigen binding receptor such as a first chimeric antigen receptor (CAR) or an endogenous or transgenic T cell receptor (TCR) directed against an antigen expressed on the surface of a target cell such as a cancer cell (then the first antigen is a tumor associated antigen) or binds to a tag that is coupled to a polypeptide such as an antibody or antigen binding fragment thereof, wherein said antibody or antigen binding fragment thereof binds to an antigen expressed on the surface of a target cell, and the boosting receptor may be a second antigen binding receptor (e.g. a second CAR) that is a chimeric costimulatory receptor (CCR) directed against a further antigen. The first antigen binding receptor may be e.g. a CAR that mediates an immune effector cell response by binding of said CAR to said first antigen expressed on the surface of a target cell or said tag. CAR constructs executing such immune effector cell responses are well-known in the art. The chimeric costimulatory receptor only boosts the immune response of the engineered cell that co-expresses the CAR and the CCR when said CCR is activated by binding of the CCR to the further antigen and when the CAR is activated by binding of the CAR to the antigen expressed on the surface of a target cell or to the tag. It is a surprising finding that the boosting effect of the CCR is obtained by a special module design of the second antigen binding receptor, the CCR. The further antigen may be also expressed on the surface of the target cell, e.g. it may be a tumor associated antigen, or the further antigen may be expressed on the surface of a second target cell, wherein said second target cell is preferentially not in a disease state, e.g. the second target cell is a B cell expressing said further antigen, e.g. CD20. Alternatively, the further antigen is an antigen that is not expressed on the surface of a (target) cell, e.g. it is a dextran. The administration of dextran to a subject in need to be treated with immune cells as disclosed herein may allow for a controlled and sustained immune response of these cells also in an inhospitable tumor environment or may reactivate said gene-modified cells, e.g. in the case of a tumor recurrence. Furthermore, the activation of the co-expressed chimeric costimulatory receptor can ensure the survival of the engineered effector cell as soon as no antigen for the antigen binding receptor is present, for example via the recognition of CD20 on omnipresent B cells by the anti-CD20 CCR or via the recognition of dextran that is administered to a patient by the anti-dextran CCR.

BRIEF DESCRIPTION OF THE DRAWINGS

FIG. 1: Schematic representation of different variants of the boosting system. An immune effector cell co-expressing an antigen binding receptor directed against an antigen (AG 1) expressed on a target cell and a chimeric costimulatory receptor (CCR) directed against a) a second antigen expressed on the target cell (AG 2), b) a second antigen expressed on a second target cell (AG 3), c) CD20 expressed on B cells (AG 4), d) soluble dextran or e) a dextran-conjugated antibody that specifically recognizes an antigen expressed on the target cell (AG 2) or on a second target cell (AG 3 or AG 4). For the anti-LLE CAR boosting, the immune effector cell comprises a CAR that binds a biotinylated-antibody which is specific for an antigen expressed on a target cell (AG 1) and a CCR directed against f) an antigen expressed on the target cell (AG 2) or a dextran-conjugated antibody specific for a second antigen expressed on the target cell or g) CD20 expressed on B cells (AG 4) or a dextran-conjugated antibody that binds an antigen expressed on a second target cell (AG 3 or AG 4).

DETAILED DESCRIPTION OF THE INVENTION

Figure 2:
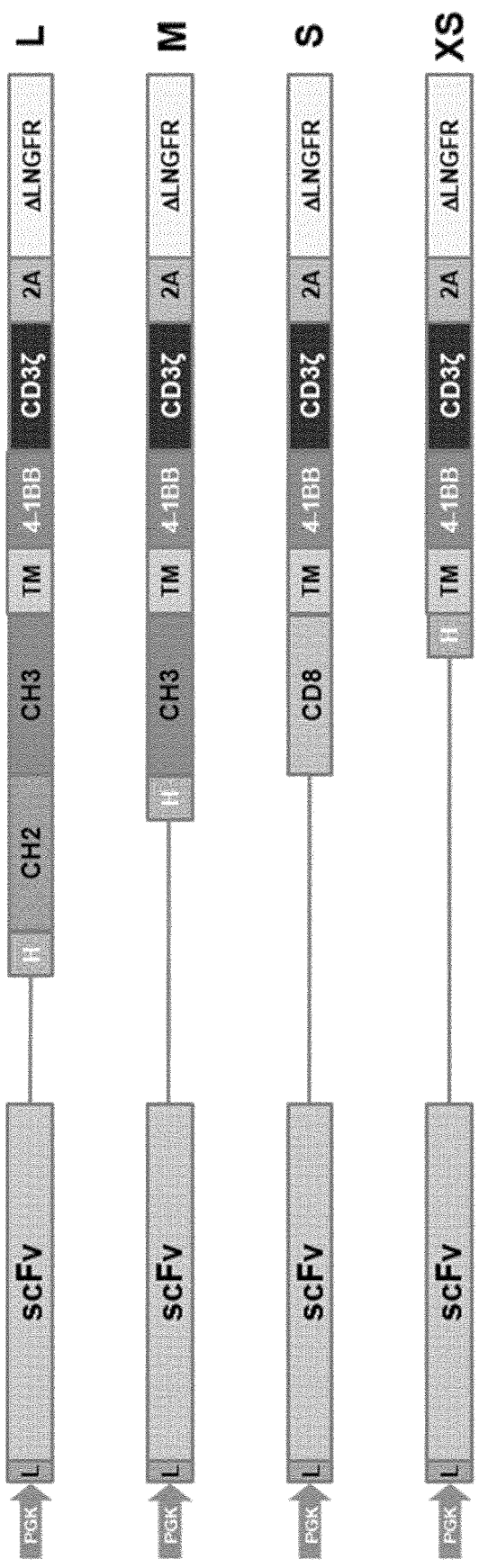
FIG. 2: Schematic representation of the different anti-HMW-MAA CAR formats. The leader sequence "L" is derived from human CD8 (SEQ ID NO: 1) or murine Igkv4 (SEQ ID NO: 2), scFvs are derived from SEQ ID NO: 3 and SEQ ID NO: 4, hinge and spacers "H" and "CH2", "CH3" and "CD8" are derived from human IgG4 or human CD8 (SEQ ID NO: 5-8), respectively. The transmembrane domain "TM" is from human CD8 (SEQ ID NO: 9), while co-stimulatory and signaling domains are from 4-1 BB (SEQ ID NO: 10) and CD3ζ (SEQ ID NO: 11). All CARs are expressed together with the marker gene ΔLNGFR linked by a 2A element (SEQ ID NO: 12).

In a first aspect the invention provides an immune effector cell comprising
  a) an antigen binding receptor, wherein said antigen binding receptor binds to a tag of a tagged polypeptide, and wherein the polypeptide of said tagged polypeptide binds to an antigen expressed on the surface of a target cell to be killed,
  and wherein the binding of said antigen binding receptor to said tag activates and stimulates an immune response of said immune effector cell thereby leading to cytotoxic activity and cytokine release of said immune effector cell,
  wherein said antigen binding receptor is a chimeric antigen receptor (CAR) comprising or consisting of an antigen binding domain, a transmembrane domain and a cytoplasmic signaling domain comprising at least one primary cytoplasmic signaling domain and at least one co-stimulatory signaling domain, wherein said antigen binding domain of said CAR binds to the tag of said tagged polypeptide, and
  b) a chimeric costimulatory receptor (CCR), wherein said CCR binds to a further antigen, wherein said further antigen is not expressed on the surface of said target cell,
  and wherein the binding of said CCR to said further antigen boosts said immune response of said immune effector cell and/or ensures survival of said immune effector cell,
  wherein said CCR comprises or consists of an antigen binding domain, a transmembrane domain and a cytoplasmic part comprising at least one co-stimulatory domain, and wherein said antigen binding domain of said CCR binds to said further antigen,
  wherein said CCR is not able to mediate said immune response on its own,
  and wherein the magnitude of enhancement of the effector response of the immune cell expressing both the CAR, and the CCR is at least 1.5 fold, at least 2 fold, at least 5 fold, at least 10 fold, at least 20 fold, at least 30 fold, at least 40 fold or at least 50 fold compared to the effector response of the immune cell that is activated and stimulated solely by the CAR, and that is not boosted by the CCR.

Said target cell may be a cancer cell or an autoimmune cell.

Said antigen expressed on the surface of a target cell may be a tumor associated antigen (TAA) and said target cell may be a cancer cell.

Said antigen binding receptor may be an antigen binding receptor that mediates a strong immune effector cell response when the receptor binds to the tag of the tagged polypeptide, i.e. said antigen binding receptor, e.g. a CAR may be a high efficacy antigen binding receptor, e.g. CAR with regard to the immune effector cell response triggered by the binding of said antigen binding receptor, e.g. CAR, to the tag. Said antigen binding receptor may bind said tag with high, medium or low affinity as long as it may trigger an immune effector cell response.

Said immune effector cell, wherein said primary cytoplasmic signaling domain of said CAR may be CD3ζ.

Said immune effector cell, wherein said cytoplasmic part of said CCR may comprise or consist of at least one co-stimulatory domain selected from the group consisting of ICOS, CD154, CD5, CD2, CD46, HVEM, CD8, CD97, TNFRSF18, CD30, SLAM, DAP10, CD64, CD16, CD89, MyD88, KIR-2DS, KIR-3DS, NKp30, NKp44, NKp46, NKG2D, ICAM, CD27, OX40, 4-1BB and CD28.

Said immune effector cell, wherein said cytoplasmic part of said CCR may comprise or consist of at least one co-stimulatory domain selected from the group consisting of ICOS, CD154, CD5, CD2, CD46, HVEM, CD8, CD97, TNFRSF18, CD30, SLAM, DAP10, CD64, CD16, CD89, MyD88, KIR-2DS, KIR-3DS, NKp30, NKp44, NKp46, NKG2D, ICAM, CD27, OX40, 4-1BB and CD28 and wherein said cytoplasmic part of said CCR does not comprise or does not consist of an ITAM containing domain such as CD3ζ or another primary cytoplasmic signaling domain.

Said immune effector cell, wherein said cytoplasmic part of said CCR may comprise or consist of at least one 4-1BB co-stimulatory domain and/or at least one CD28 co-stimulatory domain.

Said immune effector cell, wherein said cytoplasmic part of said CCR may comprise or consist of two 4-1BB co-stimulatory domains or two CD28 co-stimulatory domains.

Said cytoplasmic part of said CCR may comprise or consist of one 4-1BB co-stimulatory domain and one CD28 co-stimulatory domain.

Said immune effector cell, wherein said cytoplasmic part of said CCR as described above may comprise at least two co-stimulatory domains but no primary cytoplasmic signaling domain.

Said immune effector cell, wherein the polypeptide of said tagged polypeptide may be an antibody or antigen binding fragment thereof, wherein said antibody or antigen binding fragment thereof may bind to said antigen expressed on the surface of said target cell, and wherein the tag of said tagged polypeptide may be a hapten. Said hapten may be FITC, biotin, PE, or streptavidin.

Said immune effector cell, wherein the polypeptide of said tagged polypeptide may be an antigen binding moiety (ABM), wherein the tag of said tagged polypeptide may be a linker/label epitope (LLE) of a target cell binding molecule (TCBM), and wherein said antigen binding receptor may be an anti-linker/label epitope chimeric antigen receptor (anti-LLE CAR) comprising
  I) a linker/label epitope (LLE) binding domain,
  II) a transmembrane domain, and
  III) a cytoplasmic signaling domain comprising or consisting of at least one primary cytoplasmic signaling domain and at least one co-stimulatory signaling domain,
  wherein said extracellular LLE binding domain may bind a target cell binding molecule (TCBM) comprising
    i) an antigen binding moiety (ABM), wherein said ABM may bind specifically to said antigen expressed on the surface of said target cell,
    ii) a label moiety (LaM), wherein said LaM is a naturally occurring molecule in a subject or a derivative thereof,
    iii) a linker moiety (LiM) conjugating said ABM and said LaM, thereby forming a linker/label epitope (LLE),
  wherein said extracellular LLE binding domain binds said LLE with a higher preference than said naturally occurring molecule.

Said extracellular LLE binding domain may bind with an at least twofold higher affinity to said LLE than to said naturally occurring molecule.

The k(off) value for the binding between said extracellular LLE binding domain may be higher to a monomeric LLE and said naturally occurring molecule than to a multimeric LLE. Said naturally occurring molecule may be in the circulatory system of said subject.

Said LLE may be generated site-specifically, thereby forming an epitope comprising a part of said LaM and a part of said LiM.

Said LaM may be selected from the group consisting of amino acids, peptides, proteins, creatinine, biotin, biocytin, lipids, hormones, vitamins, carbohydrates or a derivative thereof.

Said LiM may be a molecule capable of generating said LLE.

Said LiM may be selected from the group consisting of peptides, proteins, nucleic acids, carbohydrates, polyhydroxyalkanoates, alkyl chains, alkanoic acids, carboxylic acids, farnesyls, polyethylene glycols, lipids or a derivative thereof.

Said LaM may be biotin or a derivative thereof and said LiM may be a 6-(6-aminohexanamido) hexanoyl moiety or a 6-aminohexanoyl moiety.

Said extracellular LLE binding domain may comprise the sequence of SEQ ID NO: 17 and SEQ ID NO: 18.

Said ABM may be an antibody or an antigen binding fragment thereof.

Said anti-LLE CAR may comprise the sequence of SEQ ID NO: 22 and SEQ ID NO: 23, and wherein said extracellular LLE binding domain binds to a 6-[6-(biotinamido) hexanamido] hexanoyl moiety.

Said immune effector cell, wherein said further antigen may be expressed on the surface of another cell than the target cell.

Said immune effector cell, wherein said further antigen may be expressed on the surface of another cell than the target cell that is not in a disease state.

Said other cell may be a (hematopoietic) cell. Said second target cell may be a B cell. Said other cell may be a second cancer cell, i.e. a different type of cancer cell than the first target/cancer cell.

Said immune effector cell, wherein said further antigen is CD20 and said other cell is a B cell. Preferentially said B cell is not in a disease state. The benefit of CD20 as said further antigen and a B cell said other cell is the omnipresence of B cells expressing CD20 in the circulatory system of a subject.

Said immune effector cell, wherein said antigen binding domain of said CCR may comprise the amino acid sequence of SEQ ID NO: 13, and wherein said cytoplasmic part of said CCR may comprise or consists of the amino acid sequence of SEQ ID NO: 21.

Said immune effector cell, wherein said further antigen is not expressed on the surface of a cell.

Said immune effector cell, wherein said further antigen may be dextran. Said dextran may be unbound dextran, i.e. free dextran, soluble dextran or dextran conjugated to colloidal nano- or microparticles. Said dextran may be administered to a patient in need thereof that harbours the immune effector cell as disclosed herein to boost said immune effector cell under controllable conditions. Alternatively, said dextran may be coupled to an antibody or antigen binding fragment thereof, wherein said antibody may bind specifically to another antigen that may be expressed on said target cell or on said other cell.

Said immune effector cell, wherein said antigen binding domain of said CCR may comprise the amino acid sequence of SEQ ID NO: 19, and wherein said cytoplasmic part may comprise or consist of the amino acid sequence of SEQ ID NO: 21.

In a further aspect the invention provides an immune effector cell comprising
  a) an antigen binding receptor, wherein said antigen binding receptor binds to a tag of a tagged polypeptide, and wherein the polypeptide of said tagged polypeptide binds to an antigen expressed on the surface of a target cell to be killed,
  and wherein the binding of said antigen binding receptor to said tag activates and stimulates an immune response of said immune effector cell thereby leading to cytotoxic activity and cytokine release of said immune effector cell;
  wherein said antigen binding receptor is a chimeric antigen receptor (CAR) comprising an antigen binding domain, a transmembrane domain and a cytoplasmic signaling domain comprising at least one primary cytoplasmic signaling domain and at least one co-stimulatory signaling domain, wherein said antigen binding domain of said CAR binds to the tag of said tagged polypeptide, and
  b) a chimeric costimulatory receptor (CCR), wherein said CCR binds to a further antigen, wherein said further antigen is expressed on the surface of
    i) said target cell to be killed, and
    ii) another cell than the target cell
  and wherein the binding of said CCR to said further antigen boosts said immune response of said immune effector cell and/or ensures survival of said immune effector cell,
  wherein said CCR comprises an antigen binding domain, a transmembrane domain and a cytoplasmic part comprising at least one co-stimulatory domain, and wherein said antigen binding domain of said CCR binds to said further antigen, wherein said CCR is not able to mediate said immune response on its own, and wherein the magnitude of enhancement of the effector response of the immune cell expressing both the CAR, and the CCR is at least 1.5 fold, at least 2 fold, at least 5 fold, at least 10 fold, at least 20 fold, at least 30 fold, at least 40 fold or at least 50 fold compared to the effector response of the immune cell that is activated and stimulated solely by the CAR, and that is not boosted by the CCR.

Said target cell may be a cancer cell or an autoimmune cell.

Said antigen expressed on the surface of a target cell may be a tumor associated antigen (TAA) and said target cell may be a cancer cell.

Said antigen binding receptor may be an antigen binding receptor that mediates a strong immune effector cell response when the receptor binds to the tag of the tagged polypeptide, i.e. said antigen binding receptor, e.g. a CAR may be a high efficacy antigen binding receptor, e.g. CAR with regard to the immune effector cell response triggered by the binding of said antigen binding receptor, e.g. CAR, to the tag. Said antigen binding receptor may bind said tag with high, medium or low affinity as long as it may trigger an immune effector cell response.

Said immune effector cell, wherein said primary cytoplasmic signaling domain of said CAR may be CD3ζ.

Said immune effector cell, wherein said cytoplasmic part of said CCR may comprise or consist of at least one co-stimulatory domain selected from the group consisting of ICOS, CD154, CD5, CD2, CD46, HVEM, CD8, CD97, TNFRSF18, CD30, SLAM, DAP10, CD64, CD16, CD89, MyD88, KIR-2DS, KIR-3DS, NKp30, NKp44, NKp46, NKG2D, ICAM, CD27, OX40, 4-1BB and CD28.

Said immune effector cell, wherein said cytoplasmic part of said CCR may comprise or consist of at least one co-stimulatory domain selected from the group consisting of ICOS, CD154, CD5, CD2, CD46, HVEM, CD8, CD97, TNFRSF18, CD30, SLAM, DAP10, CD64, CD16, CD89, MyD88, KIR-2DS, KIR-3DS, NKp30, NKp44, NKp46, NKG2D, ICAM, CD27, OX40, 4-1BB and CD28 and wherein said cytoplasmic part of said CCR does not comprise or does not consist of an ITAM containing domain such as CD3ζ or another primary cytoplasmic signaling domain.

Said immune effector cell, wherein said cytoplasmic part of said CCR may comprise or consist of at least one 4-1BB co-stimulatory domain and/or at least one CD28 co-stimulatory domain.

Said immune effector cell, wherein said cytoplasmic part of said CCR may comprise or consist of two 4-1BB co-stimulatory domains or two CD28 co-stimulatory domains.

Said cytoplasmic part of said CCR may comprise or consist of one 4-1BB co-stimulatory domain and one CD28 co-stimulatory domain.

Said immune effector cell, wherein said cytoplasmic part of said CCR as described above may comprise at least two co-stimulatory domains but no primary cytoplasmic signaling domain.

Said immune effector cell, wherein the polypeptide of said tagged polypeptide may be an antibody or antigen binding fragment thereof, wherein said antibody or antigen binding fragment thereof may bind to said antigen expressed on the surface of said target cell, and wherein the tag of said tagged polypeptide may be a hapten. Said hapten may be FITC, biotin, PE, or streptavidin.

Said immune effector cell, wherein the polypeptide of said tagged polypeptide may be an antigen binding moiety (ABM), wherein the tag of said tagged polypeptide may be a linker/label epitope (LLE) of a target cell binding molecule (TCBM), and wherein said antigen binding receptor may be an anti-linker/label epitope chimeric antigen receptor (anti-LLE CAR) as disclosed above and herein.

Said immune effector cell, wherein said further antigen that may be expressed on the surface of said other cell than the target cell is not in a disease state.

In a further aspect the invention provides an immune effector cell comprising a) an antigen binding receptor, wherein said antigen binding receptor binds to a tumor associated antigen expressed on the surface of a target cell, wherein said target cell is a cancer cell,
and wherein the binding of said antigen binding receptor to said tumor associated antigen activates and stimulates an immune response of said immune effector cell;
wherein said antigen binding receptor is a chimeric antigen receptor (CAR) comprising or consisting of an antigen binding domain, a transmembrane domain and a cytoplasmic signaling domain comprising at least one primary cytoplasmic signaling domain and at least one co-stimulatory signaling domain, wherein said antigen binding domain of said CAR binds to the tumor associated antigen,
and
b) a chimeric costimulatory receptor (CCR), wherein said CCR binds to a further antigen, wherein said further antigen is CD20 or is not expressed on a surface of a cell,
and wherein the binding of said CCR to said further antigen boosts said immune response of said immune effector cell and/or ensures survival of said immune effector cell,
wherein said CCR comprises or consists of an antigen binding domain, a transmembrane domain and cytoplasmic part comprising at least one co-stimulatory domain, and wherein said antigen binding domain of said CCR binds to said further antigen,
wherein said CCR is not able to mediate said immune response on its own, and wherein the magnitude of enhancement of the effector response of the immune cell expressing both the CAR, and the CCR is at least 1.5 fold, at least 2 fold, at least 5 fold, at least 10 fold, at least 20 fold, at least 30 fold, at least 40 fold or at least 50 fold compared to the effector response of the immune cell that is activated and stimulated solely by the CAR, and that is not boosted by the CCR.

Said immune effector cell, wherein said further antigen may be CD20 and is not expressed on said target cell but on the surface of another cell than the target cell. Said other cell may be a B cell.

Said immune effector cell, wherein said antigen binding domain of said CCR may comprise the amino acid sequence of SEQ ID NO: 13, and wherein said cytoplasmic part of said CCR may comprise or consist of the amino acid sequence of SEQ ID NO: 21.

Said immune effector cell, wherein said further antigen may be CD20 and may be expressed on both said target cell and said other cell.

Said immune effector cell, wherein said further antigen that is not expressed on a surface of a cell is dextran. Said dextran may be unbound dextran, i.e. free dextran, soluble dextran or dextran conjugated to colloidal nano- or microparticles. Said dextran may be administered to a patient in need thereof that harbours the immune effector cell as disclosed herein to boost said immune effector cell under controllable conditions. Alternatively, said dextran may be coupled to an antibody or antigen binding fragment thereof, wherein said antibody may bind specifically to another antigen that may be expressed on said target cell or on said other cell.

Said immune effector cell, wherein said antigen binding domain of said CCR may comprise the amino acid sequence of SEQ ID NO: 19, and wherein said cytoplasmic part may comprise or consist of the amino acid sequence of SEQ ID NO: 21.

Said antigen binding receptor may be an antigen binding receptor that mediates a strong immune effector cell response when the receptor binds to the tumor associated antigen, i.e. said antigen binding receptor, e.g. a CAR may be a high efficacy antigen binding receptor, e.g. CAR with regard to the immune effector cell response triggered by the binding of said antigen binding receptor, e.g. CAR, to the tumor associated antigen. Said antigen binding receptor may bind said TAA with high, medium or low affinity as long as it may trigger an immune effector cell response.

Said target cell may be a cancer cell of a solid tumor.

Said immune effector cell, wherein said primary cytoplasmic signaling domain of said CAR may be CD3ζ.

Said immune effector cell, wherein said cytoplasmic part of said CCR may comprise or consist of at least one co-stimulatory domain selected from the group consisting of ICOS, CD154, CD5, CD2, CD46, HVEM, CD8, CD97, TNFRSF18, CD30, SLAM, DAP10, CD64, CD16, CD89, MyD88, KIR-2DS, KIR-3DS, NKp30, NKp44, NKp46, NKG2D, ICAM, CD27, OX40, 4-1BB and CD28.

Said immune effector cell, wherein said cytoplasmic part of said CCR may comprise or consist of at least one co-stimulatory domain selected from the group consisting of ICOS, CD154, CD5, CD2, CD46, HVEM, CD8, CD97, TNFRSF18, CD30, SLAM, DAP10, CD64, CD16, CD89, MyD88, KIR-2DS, KIR-3DS, NKp30, NKp44, NKp46, NKG2D, ICAM, CD27, OX40, 4-1BB and CD28 and wherein said cytoplasmic part of said CCR does not comprise or does not consist of an ITAM containing domain such as CD3ζ or another primary cytoplasmic signaling domain.

Said immune effector cell, wherein said cytoplasmic part of said CCR may comprise or consist of at least one 4-1BB co-stimulatory domain and/or at least one CD28 co-stimulatory domain.

Said immune effector cell, wherein said cytoplasmic part of said CCR may comprise or consist of two 4-1BB co-stimulatory domains or two CD28 co-stimulatory domains.

Said cytoplasmic part of said CCR may comprise or consist of one 4-1BB co-stimulatory domain and one CD28 co-stimulatory domain.

Said immune effector cell, wherein said cytoplasmic part of said CCR as described above may comprise at least two co-stimulatory domains but no primary cytoplasmic signaling domain.

In a further aspect the invention provides an immune effector cell as disclosed herein for use in immunotherapy (cell therapy) or for treatment of a disorder in a patient.

In another aspect the invention provides one or more isolated nucleic acid molecules encoding an antigen binding receptor as disclosed herein and a CCR as disclosed herein.

In a further aspect the invention provides an immunotherapy composition comprising a cell expressing an antigen binding receptor as disclosed herein and a CCR as disclosed herein.

In another aspect the invention provides an immunotherapy composition comprising one or more isolated nucleic acid molecules encoding an antigen binding receptor as disclosed herein and a CCR as disclosed herein.

In one aspect the invention provides a method of treating a disorder in a subject comprising the step of administering to the subject one or more therapeutically effective populations of immune effector cells co-expressing the antigen binding receptor as disclosed herein and the CCR as disclosed herein.

Said method may comprise the additional step of administering to the subject one or more formulations of a tagged polypeptide that is bound by said antigen binding receptor.

Said method, wherein said more formulations of tagged polypeptides are the same or different formulations of tagged polypeptides.

Or said method may comprise the addition step of administering to the subject one or more formulations of dextran (e.g. Deltadex; Dextran 40 10% in NaCl; infusion of e.g 1.5 g dextran per kg bodyweight or less) that is bound by the CCR that binds to dextran.

Said method, wherein said more therapeutically effective populations of immune cells co-expressing the antigen binding receptor as disclosed herein and the CCR as disclosed herein are the same or different populations of immune cells co-expressing the antigen binding receptor as disclosed herein and the CCR as disclosed herein.

Said method, wherein said antigen binding receptor of said more therapeutically effective populations are the same or different antigen binding receptors, or wherein said CCR of said more therapeutically effective populations are the same or different CCRs.

Said method, wherein said administering of said more formulations of one or more formulations of a tagged polypeptide that is bound by said antigen receptor to a subject in need of treatment are administered simultaneously or subsequently.

Said method, wherein said administering of said more therapeutically effective populations of immune cells co-expressing the antigen binding receptor as disclosed herein and the CCR as disclosed herein are administered simultaneously or subsequently.

Said one or more formulations of a tagged polypeptide that is bound by said antigen receptor may be administered to the subject prior, simultaneously or after administering to the subject said one or more therapeutically effective populations of immune cells co-expressing the antigen binding receptor as disclosed herein and the CCR as disclosed herein.

Said one or more formulations of a tagged polypeptide that is bound by antigen binding receptor may be replaced by one or more therapeutically effective populations of (hematopoietic) cells that express said antigen on their cell surface Said method, wherein said administering of said more formulations of one or more formulations of dextran that is bound by CCR to a subject in need of treatment are administered simultaneously or subsequently.

Said one or more formulations of dextran that is bound by said CCR may be administered to the subject prior, simultaneously or after administering to the subject said one or more therapeutically effective populations of immune cells co-expressing the antigen binding receptor as disclosed herein and the CCR as disclosed herein.

The DNA or RNA construct(s) (nucleic acid molecule(s)) encoding the antigen binding receptor as disclosed herein and the CCR as disclosed herein ("encoding the boosting system as disclosed herein") can be transfected or transduced into a host cell by methods well known in the art (e.g. viral-based systems including retrovirus and lentivirus, physical methods including electroporation, biological methods, chemical methods). Regardless the methods used to integrate, preferentially stably integrate, the DNA encoding the antigen binding receptor as disclosed herein and the CCR as disclosed herein, in the host cell, as a result the host cell expresses the antigen binding receptor as disclosed herein and the CCR as disclosed herein. Alternatively, the nucleic acid sequences may be produced synthetically.

An engineered cell expressing the antigen binding receptor as disclosed herein and the CCR as disclosed herein may be isolated (enriched or separated) after the transfection/transduction process for generating such an engineered cell from non-transfected/transduced cells by methods well known in the art, e.g. fluorescent based separating technologies such as FACS® or magnetic cell separation methods such as MACS® (Miltenyi Biotec GmbH).

Generally, the cells such as immune cells, preferentially T cells for generating engineered cells expressing the antigen binding receptor as disclosed herein and the CCR as disclosed herein may be obtained from a subject. Cells such as immune cells, preferentially T cells, can be obtained from a variety of sources such as peripheral blood mononuclear cells (PMBCs), bone marrow, lymph node tissue, cord blood or thymus tissue. For enrichment of these cells methods well known in the art can be used such as centrifugation through a Ficoll™ or PERCOLL™ gradient or positive/negative selection techniques such as fluorescent sorting (e.g. FACS-sort) or magnetic sorting (e.g. MACS®).

Preferably the enriched cell population comprises at least about 90% of the selected cell type. In particular aspects, the cell population comprises at least about 90%, 91%, 92%, 93%, 94%, 95%, 96%, 97%, 98%, 99%, or even 100% of the selected cell type.

Exemplary, T cells of a blood sample of a subject are magnetically labelled, for example with a magnetic bead coupled to antibodies specific for CD4, washed, magnetically enriched and collected. Then these T cells may be engineered to express the antigen binding receptor as disclosed herein and the CCR as disclosed herein on their cell surface.

In one embodiment of the invention the isolated/enriched engineered cell such as immune cells, preferentially T cells expressing the antigen binding receptor as disclosed herein and the CCR as disclosed herein may be activated prior or after genetic modification and expanded to increase the number of engineered (T) cells using methods well known in the art, for example polyclonal stimulation of T cells with the TransAct T Cell Reagent (Miltenyi Biotec; WO2014048920A1) that consists of a colloidal nanomatrix conjugated to humanized CD3 and CD28 agonists. Preferentially, said number of engineered cells such as immune cells, e.g. T cells, may be increased to a therapeutically effective amount.

A cell expressing the antigen binding receptor as disclosed herein and the CCR as disclosed herein may be engineered by a RNA encoding the antigen binding receptor as disclosed herein and the CCR as disclosed herein. The RNA may be transfected or transduced into a host cell by methods well known in the art (e.g. viral-based systems, physical methods, biological methods, chemical methods). Regardless the methods used to transfer the RNA encoding the antigen binding receptor as disclosed herein and the CCR as disclosed herein into the host cell, as a result the host cell expresses the antigen binding receptor as disclosed herein and the CCR as disclosed herein. "RNA-engineered cells" express the antigen binding receptor as disclosed herein and the CCR as disclosed herein for a limited time (transient expression).

The genetically modified (immune) cells expressing the antigen binding receptor as disclosed herein and the CCR as disclosed herein, preferentially T cells, may be generated in an automated process in a closed system. A process for the generation of genetically modified cells, preferentially T cells, may comprise e.g. the steps:
 a) providing a cell sample comprising (immune) cells
 b) preparation of the cell sample by centrifugation
 c) magnetic separation of the (immune) cells, preferentially T cells,
 d) activation of the enriched (immune) cells, preferentially T cells, using modulatory agents
 e) genetically modifying the (immune) cells, preferentially T cells, to express the antigen binding receptor as disclosed herein and the CCR as disclosed herein
 f) expansion of the genetically modified (immune) cells, preferentially T cells, in a cultivation chamber
 g) washing of the cultured (immune) cells, preferentially T cells.

All these steps may be performed automatically in a closed system, preferentially in a closed and sterile system.

The process is especially suited for preparing gene modified cells such as immune cells, preferentially T cells, wherein the enriched (immune) cells, preferentially T cells, are gene-modified by using viral and/or non-viral vectors.

Any of these steps may be multiplied, omitted or may occur in a different order.

The modulatory agents may be selected from agonistic antibodies and/or cytokines.

The gene-modified (immune) cells, preferentially T cells, may be enriched by magnetic labelling of (immune) cells and magnetic separation before or after cultivation to obtain higher frequency of gene-modified (immune) cells, preferentially T cells, in the final cellular product. As a closed and sterile system for cell modification, the fully automated cell processing device CliniMACS Prodigy® and associated tubing sets (Miltenyi Biotec GmbH, Germany) may be used (WO2009/072003). This closed system meets the requirements of GMP-grade processing of almost any kind of cellular products and may allow reducing clean room requirements, improve technology transfer and harmonization of cell manufacturing processes.

In one embodiment of the invention, the boosting system as disclosed herein may be for use in the treatment in a subject suffering from a disorder such as cancer. Cells such as immune cells, e.g. T cells of a subject, may be isolated or established immune cell lines may be used. The subject may suffer from said disorder such as cancer (a patient) or may be a healthy subject. These immune cells are genetically modified in vitro to express the CAR that binds to a tag as disclosed herein and the CCR as disclosed herein. These engineered cells may be activated and expanded in vitro to a therapeutically effective population of cells expressing the CAR that binds to a tag as disclosed herein and the CCR as disclosed herein. In cellular therapy these engineered cells may be infused to a recipient in need thereof as a pharmaceutical composition (or a formulation of a therapeutically effective population of cells expressing the CAR that binds to a tag as disclosed herein and the CCR as disclosed herein), in addition to a second pharmaceutical composition, a formulation of hapten or TCBM. The infused cells in the recipient may be able to kill (or at least stop growth of) cancerous cells expressing the antigen which is recognized by the boosting system as disclosed herein. The CCR boosts the immune response of the genetically modified cell when it becomes activated by binding to the further antigen. This further antigen might by CD20 that is expressed on B cells or may be dextran that is applied in a controllable manner to the subject. The recipient may be the same subject from which the cells were obtained (autologous cell therapy) or may be from another subject of the same species (allogeneic cell therapy).

The therapeutically effective population of cells expressing the CAR that binds to a tag as disclosed herein and the CCR as disclosed herein may be administered to the patient before the administration of the formulation of hapten or TCBM to the subject. Alternatively, the formulation of hapten or TCBM may be administered to the subject before or at the same time as the administration the therapeutically effective population of cells expressing the CAR that binds to ma tag as disclosed herein and the CCR as disclosed herein to the subject. A further variation includes in vitro culturing the therapeutically effective population of cells expressing the CAR that binds to a tag as disclosed herein and the CCR as disclosed herein with the hapten or TBCM of the formulation of hapten or TCBM prior to administration to the subject.

The therapeutically effective population of cells expressing the CAR that binds to an antigen such as a tumor associated antigen as disclosed herein and the CCR that binds to dextran as disclosed herein may be administered to the patient before the administration of the formulation of dextran to the subject. Alternatively, the formulation of dextran may be administered to the subject before or at the same time as the administration the therapeutically effective population of cells expressing the CAR that binds to the antigen such as a tumor associated antigen as disclosed herein and the CCR that binds to dextran as disclosed herein to the subject. A further variation includes in vitro culturing the therapeutically effective population of cells expressing the CAR that binds to the antigen such as a tumor associated antigen as disclosed herein and the CCR that binds to dextran as disclosed herein with the dextran of the formulation of dextran prior to administration to the subject.

Populations of cells expressing the antigen binding receptor as disclosed herein and the CCR as disclosed herein may be formulated for administered to a subject using techniques known to the skilled artisan.

Formulations comprising therapeutically effective population(s) of cells expressing the antigen binding receptor as disclosed herein and the CCR as disclosed herein may include pharmaceutically acceptable excipient(s) (carrier or diluents). Excipients included in the formulations will have different purposes depending, for example, on the nature of the antigen binding domain of the CAR and CCR as disclosed herein, the (sub) population of immune cells used, and the mode of administration. Examples of generally used excipients include, without limitation: saline, buffered saline, dextrose, water-for-injection, glycerol, ethanol, and combinations thereof, stabilizing agents, solubilizing agents and surfactants, buffers and preservatives, tonicity agents, bulking agents, and lubricating agents.

A formulation of a therapeutically effective population(s) of cells expressing the antigen binding receptor as disclosed herein and the CCR as disclosed herein may include one population of cells expressing the antigen binding receptor as disclosed herein and the CCR as disclosed herein, or more than one population of cells expressing the antigen binding receptor as disclosed herein and the CCR as disclosed herein. The different populations of cells expressing the antigen binding receptor as disclosed herein and the CCR as disclosed herein may vary based on the identity of the antigen binding domain, the identity of the activation domain, the identity of the (sub) population of immune cells, or a combination thereof.

The formulations comprising therapeutically effective population(s) of cells expressing the antigen binding receptor as disclosed herein and the CCR as disclosed herein may be administered to a subject using modes and techniques known to the skilled artisan. Exemplary modes include, but are not limited to, intravenous injection. Other modes include, without limitation, intratumoral, intradermal, subcutaneous (s.c, s.q., sub-Q, Hypo), intramuscular (i.m.), intraperitoneal (i.p.), intra-arterial, intramedulary, intracardiac, intra-articular (joint), intrasynovial (joint fluid area), intracranial, intraspinal, and intrathecal (spinal fluids).

The formulations comprising therapeutically effective population(s) of cells expressing the antigen binding receptor as disclosed herein and the CCR as disclosed herein that are administered to a subject comprise a number of cells expressing the antigen binding receptor as disclosed herein and the CCR as disclosed that is effective for the treatment of the specific indication or cancer.

In general, formulations may be administered that comprise between about $1\times10^4$ and about $1\times10^{10}$ cells expressing the antigen binding receptor as disclosed herein and the CCR as disclosed herein. In most cases, the formulation may comprise between about $1\times10^5$ and about $1\times10^9$ cells, expressing the antigen binding receptor as disclosed herein and the CCR as disclosed herein, from about $5\times10^5$ to about $5\times10^8$ cells expressing the antigen binding receptor as disclosed herein and the CCR as disclosed herein, or from about $1\times10^6$ to about $1\times10^7$ cells expressing the antigen binding receptor as disclosed herein and the CCR as disclosed herein. However, the number of cells expressing the antigen binding receptor as disclosed herein and the CCR as disclosed administered to a subject may vary between wide limits, depending upon the location, source, identity, extent and severity of the disorder, the age and condition of the individual to be treated, etc. A physician may ultimately determine appropriate dosages to be used.

The haptens or TCBMs or dextran may be formulated for administered to a subject using techniques known to the skilled artisan. Formulations of the haptens or TCBMs or dextran may include pharmaceutically acceptable excipient(s) (carriers or diluents). Excipients included in the formulations will have different purposes depending, for example, on the nature of the label moiety, the linker moiety, the ABM, the hapten and the mode of administration. Examples of generally used excipients include, without limitation: saline, buffered saline, dextrose, water-for-injection, glycerol, ethanol, and combinations thereof, stabilizing agents, solubilizing agents and surfactants, buffers and preservatives, tonicity agents, bulking agents, and lubricating agents.

A formulation of hapten or TCBM may include one type of hapten or TCBM, or more than one type of hapten or TCBM. The different types of TCBMs may vary based on the identity of the label moiety, the linker moiety, the antigen binding moiety, or a combination thereof in the case of TCBMs.

The haptens or TCBMs or dextran may be administered to a subject using modes and techniques known to the skilled artisan. Exemplary modes include, but are not limited to, intravenous, intraperitoneal, and intratumoral injection. Other modes include, without limitation, intradermal, subcutaneous (s.c, s.q., sub-Q, Hypo), intramuscular (i.m.), intra-arterial, intramedulary, intracardiac, intra-articular (joint), intrasynovial (joint fluid area), intracranial, intraspinal, and intrathecal (spinal fluids).

Formulations comprising the haptens or TCBM or dextran are administered to a subject in an amount which is effective for treating the specific indication or disorder. In general, formulations comprising at least about 1 µg/kg to about 100 mg/kg body weight of the hapten or TCBM or dextran may be administered to a subject in need of treatment. In most cases, the dosage may be from about 100 µg/kg to about 10 mg/kg body weight of the hapten or TCBM or dextran daily, taking into account the routes of administration, symptoms, etc. However, the amount of hapten or TCBM or dextran in formulations administered to a subject may vary between wide limits, depending upon the location, source, identity, extent and severity of the disorder, the age and condition of the individual to be treated, etc. A physician may ultimately determine appropriate dosages to be used.

Embodiments

In addition to above described applications of the boosting system as disclosed herein, further embodiments of the invention are described in the following without intention to be limited to these embodiments.

In one embodiment of the invention the antigen binding receptor is a CAR or TCR (endogenous or transgenic TCR) as disclosed herein. The antigen binding receptor and the CCR as disclosed herein are expressed on the cell surface of an immune cell. The antigen binding receptor is directed against a tumor associated antigen (antigen=AG) expressed on the surface of a target cell, whereas the CCR is targeting a further (second) antigen, on the same target cell (so called cis-approach) (FIG. 1a). Activating the CCR by binding of the further antigen, e.g. a TAA, to said CCR leads to an increased co-stimulation, i.e. a boosting effect, which is associated with an improved target cell killing, induced by the CAR.

In another embodiment of the invention the first antigen binding receptor is a CAR or TCR (endogenous or transgenic TCR) as disclosed herein. The antigen binding receptor and the CCR as disclosed herein are expressed on the cell surface of an immune cell. The antigen binding receptor is directed against a defined AG (a tumor associated antigen) on a target cell, i.e. a cancer cell, whereas the CCR is directed against a second AG expressed on a second target cell (FIG. 1b), e.g. or CD20 expressed on B cells (trans-approach) (FIG. 1c). In both cases, the trans-boosting system enables a non-tumor associated co-stimulation that leads to an increased T cell cytotoxicity against the tumor cells upon the activation of both antigen binding receptor and CCR.

In another embodiment of the invention the antigen binding receptor is a CAR or TCR (endogenous or transgenic TCR) as disclosed herein. The antigen binding receptor and the CCR as disclosed herein are expressed on the cell surface of an immune cell. The antigen binding receptor is directed against a defined AG (a tumor associated antigen) on a target cell, i.e. a cancer cell, whereas the CCR is specific for dextran (FIG. 1d). The dextran is not bound to the surface of a cell. In doing so, for instance, the CAR induced T cell response against the target cell may be boosted via the CCR recognizing dextran, administered to the patient.

In another embodiment of the invention the antigen binding receptor is a CAR or TCR (endogenous or transgenic TCR) as disclosed herein. The antigen binding receptor and the CCR as disclosed herein are expressed on the cell surface of an immune cell. The antigen binding receptor is directed against a defined AG (a tumor associated antigen) on a target cell, whereas the CCR specifically recognizes a dextran-conjugated antibody or antigen binding fragment thereof (Dextran-AB) that binds an antigen (e.g. tumor associated antigen) expressed on the target cell or a second antigen expressed on a second target cell (FIG. 1e). By this means, T cell cytotoxicity may be improved via the injection of a dextran-conjugated antibody to patients which activates the CCR upon binding, leading to a heightened activation and stimulation status of the engineered T cells.

In another embodiment of the invention, the antigen binding receptor is a CAR as disclosed herein. The CAR and the CCR as disclosed herein are expressed on the cell surface of an immune cell. Here, the CAR is directed against a tagged-AB specific for an AG (a tumor associated antigen) expressed on the target cell and the CCR binds an antigen (e.g. tumor associated antigen) expressed on the target cell or a dextran-conjugated antibody, specific for a second AG expressed on the target cell (FIG. 1f) or CD20 expressed on a B cell or a dextran-conjugated antibody, specific for a second AG expressed on a second target cell (FIG. 1g). This so-called universal CAR-approach defines a platform that may enable the treatment of several kinds of cancers that differ with regard to their expressed AGs. For instance, Tumor A may be treated with a first CAR as disclosed herein in combination with Hapten-AB A binding a defined antigen expressed on Tumor A, while Tumor B may be treated with the same CAR as disclosed herein, however, in combination with Hapten-AB B binding a defined antigen expressed on Tumor B. The T cell cytotoxicity of both combinations, a CAR with Hapten-AB A as well as B may be enhanced via the CCR binding to CD20 on B cells or a dextran-conjugated antibody that can be directed against an AG expressed on the target cell or on a second target cell.

The boosting system as disclosed herein may be expressed in a cell such as an immune (effector) cell to target an antigen of a target cell such as a cancer cell for treating the disorder, e.g. cancer (tumor). Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the boosting system as disclosed herein include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Examples of hematological cancers include leukemias, including acute leukemias (such as acute lymphocytic leukemia, acute myelocytic leukemia, acute myelogenous leukemia and myeloblasts, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyo sarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

The boosting system as disclosed herein may be expressed in an immune effector cell to target an antigen associated with a virus, bacteria, parasite, or other infection in order to treat the infection.

The boosting system as disclosed herein may be expressed in cell such as an immune cell to target a self-antigen to treat an autoimmune disorder.

Definitions

Unless defined otherwise, technical and scientific terms used herein have the same meaning as commonly understood by one of ordinary skill in the art to which this invention belongs.

The term "antigen binding receptor" as used herein refers to a receptor that is expressed on the cell surface of a cell, has an antigen binding domain, a transmembrane domain and a cytoplasmic signaling domains. Examples for such antigen binding receptors are chimeric antigen receptors (CARs), T cell receptors (TCRs), both endogenous and transgenic TCRs, or killer cell immunoglobulin-like receptors (KIRs).

In general, a CAR may comprise an extracellular domain (extracellular part) comprising the antigen binding domain, a transmembrane domain and a cytoplasmic signaling domain (intracellular signaling domain). The extracellular domain may be linked to the transmembrane domain by a linker. The extracellular domain may also comprise a signal peptide. In some embodiments of the invention the antigen binding domain of a CAR binds a hapten that is coupled to a polypeptide ("haptenylated" or "tagged" polypeptide), wherein the polypeptide may bind to a tumor associated antigen. Such a CAR may be also named "anti-tag" CAR as disclosed e.g. in U.S. Pat. No. 9,233,125B2. In other embodiments of the invention, the extracellular part of the CAR may comprise a linker/label epitope (LLE) binding domain as antigen binding domain that binds to a linker/label epitope (LLE) that is part of a TCBM. Such a CAR may be named anti-LLE CAR as disclosed in the European patent application no. EP16196487.9. Both types of CARs are universal and/or adaptable CAR. Both the hapten(s) and the LLE are "tags" that are coupled directly or indirectly to a polypeptide (the tagged polypeptide), wherein the polypeptide may bind to a tumor associated antigen expressed on the (cell) surface of a target cell.

A "signal peptide" refers to a peptide sequence that directs the transport and localization of the protein within a cell, e.g. to a certain cell organelle (such as the endoplasmic reticulum) and/or the cell surface.

Generally, an "antigen binding domain" refers to the region of the CAR that specifically binds to an antigen. The CARs of the invention may comprise one or more antigen binding domains. Generally, the targeting regions on the CAR are extracellular. The antigen binding domain may comprise an antibody or an antigen binding fragment thereof. The antigen binding domain may comprise, for example, full length heavy chain, Fab fragments, single chain Fv (scFv) fragments, divalent single chain antibodies or diabodies. Any molecule that binds specifically to a given antigen such as affibodies or ligand binding domains from naturally occurring receptors may be used as an antigen binding domain. Often the antigen binding domain is a scFv. Normally, in a scFv the variable regions of an immunoglobulin heavy chain and light chain are fused by a flexible linker to form a scFv. Such a linker may be for example the "$(G_4/S)_3$-linker".

In some instances, it is beneficial for the antigen binding domain to be derived from the same species in which the CAR will be used in. For example, when it is planned to use it therapeutically in humans, it may be beneficial for the antigen binding domain of the CAR to comprise a human or humanized antibody or antigen binding fragment thereof. Human or humanized antibodies or antigen binding fragments thereof can be made by a variety of methods well known in the art. In some embodiments of the invention the CAR as disclosed herein has an extracellular linker/label epitope binding domain as an antigen binding domain allowing to bind indirectly via a target cell binding molecule as disclosed herein to an antigen expressed on the surface of a target cell.

"Spacer" or "hinge" as used herein refers to the hydrophilic region which is between the antigen binding domain and the transmembrane domain. The CARs of the invention may comprise an extracellular spacer domain but is it also possible to leave out such a spacer. The spacer may include e.g. Fc fragments of antibodies or fragments thereof, hinge regions of antibodies or fragments thereof, CH2 or CH3 regions of antibodies, accessory proteins, artificial spacer sequences or combinations thereof. A prominent example of a spacer is the CD8alpha hinge. The transmembrane domain of the CAR may be derived from any desired natural or synthetic source for such domain. When the source is natural the domain may be derived from any membrane-bound or transmembrane protein. The transmembrane domain may be derived for example from CD8alpha or CD28. When the key signaling and antigen recognition modules (domains) are on two (or even more) polypeptides then the CAR may have two (or more) transmembrane domains. The splitting key signaling and antigen recognition modules enable for a small molecule-dependent, titratable and reversible control over CAR cell expression (Wu et al, 2015, Science 350: 293-303) due to small molecule-dependent heterodimerizing domains in each polypeptide of the CAR.

The cytoplasmic signaling domain (or the intracellular signaling domain) of the CAR is responsible for activation of at least one of the normal effector functions of the immune cell in which the CAR is expressed. "Effector function" means a specialized function of a cell, e.g. in a T cell an effector function may be cytolytic activity or helper activity including the secretion of cytokines. The intracellular signaling domain refers to the part of a protein which transduces the effector function signal and directs the cell expressing the CAR to perform a specialized function. The intracellular signaling domain may include any complete, mutated or truncated part of the intracellular signaling domain of a given protein sufficient to transduce a signal which initiates or blocks immune cell effector functions.

Prominent examples of intracellular signaling domains for use in the CARs include the cytoplasmic signaling sequences of the T cell receptor (TCR) and co-receptors that initiate signal transduction following antigen receptor engagement.

Generally, T cell activation can be mediated by two distinct classes of cytoplasmic signaling sequences, firstly those that initiate antigen-dependent primary activation through the TCR (primary cytoplasmic signaling sequences, primary cytoplasmic signaling domain) and secondly those that act in an antigen-independent manner to provide a secondary or co-stimulatory signal (secondary cytoplasmic signaling sequences, co-stimulatory signaling domain). Therefore, an intracellular signaling domain of a CAR may comprise one or more primary cytoplasmic signaling domains and/or one or more secondary cytoplasmic signaling domains.

Primary cytoplasmic signaling domains that act in a stimulatory manner may contain ITAMs (immunoreceptor tyrosine-based activation motifs).

Examples of ITAM containing primary cytoplasmic signaling domains often used in CARs are that those derived from TCRζ (CD3ζ), FcRgamma, FcRbeta, CD3gamma, CD3delta, CD3epsilon, CD5, CD22, CD79a, CD79b, and CD66d. Most prominent is sequence derived from CD3ζ.

The cytoplasmic domain of the CAR may be designed to comprise the CD3ζ signaling domain by itself or combined with any other desired cytoplasmic domain(s). The cytoplasmic domain of the CAR can comprise a CD3ζ chain portion and a co-stimulatory signaling region (domain). The co-stimulatory signaling region refers to a part of the CAR comprising the intracellular domain of a co-stimulatory molecule. A co-stimulatory molecule is a cell surface molecule other than an antigen receptor or their ligands that is required for an efficient response of lymphocytes to an antigen. Examples for a co-stimulatory molecule are CD27, CD28, 4-1BB (CD137), OX40, CD30, CD40, PD-1, ICOS, lymphocyte function-associated antigen-1 (LFA-1), CD2, CD7, LIGHT, NKG2C, B7-H3.

The cytoplasmic signaling sequences within the cytoplasmic signaling part of the CAR may be linked to each other with or without a linker in a random or specified order. A short oligo- or polypeptide linker, which is preferably between 2 and 10 amino acids in length, may form the linkage. A prominent linker is the glycine-serine doublet.

As an example, the cytoplasmic domain may comprise the signaling domain of CD3ζ and the signaling domain of CD28. In another example the cytoplasmic domain may comprise the signaling domain of CD3ζ and the signaling domain of CD27. In a further example, the cytoplasmic domain may comprise the signaling domain of CD3ζ, the signaling domain of CD28, and the signaling domain of CD27.

As aforementioned either the extracellular part or the transmembrane domain or the cytoplasmic domain of a CAR may also comprise a heterodimerizing domain for the aim of splitting key signaling and antigen recognition modules of the CAR.

The CAR may be further modified to include on the level of the nucleic acid encoding the CAR one or more operative elements to eliminate CAR-T cells by virtue of a suicide switch. The suicide switch can include, for example, an apoptosis inducing signaling cascade or a drug that induces cell death. In one embodiment, the nucleic acid expressing and encoding the CAR can be further modified to express an enzyme such thymidine kinase (TK) or cytosine deaminase (CD).

The chimeric costimulatory receptor (CCR) is a second antigen binding receptor of the boosting system as disclosed herein and may be considered as a special kind of CAR (the second CAR of the boosting system, the other CAR of the boosting system is the first CAR when the antigen binding receptor is a CAR; generally this first CAR is named herein as "the CAR" whereas the second CAR is generally named herein as the CCR). The CCR enhances the magnitude of the effector response of the immune cell expressing both the antigen binding receptor, e.g. a CAR, and the CCR and promotes extended survival. The magnitude of enhancement of the effector response of the immune cell expressing both the antigen binding receptor, e.g. a CAR, and the CCR may be at least 1.5 fold, at least 2 fold, at least 5 fold, at least 10 fold, at least 20 fold, at least 30 fold, at least 40 fold or at least 50 fold compared to the effector response of the immune cell that is activated and stimulated solely by the antigen binding receptor, e.g. the CAR, and that is not boosted by the CCR. The increase of magnitude of effector response of the immune cell may be measured or determined e.g. by secretion of effector cytokines such as IL-2, IFN-γ, TNF-α.

For example, the amount of secretion of effector cytokines such as IL-2, IFN-γ, TNF-α by the immune cell expressing both the antigen binding receptor, e.g. a CAR, and the CCR may be at least 1.5 fold, at least 2 fold, at least 5 fold, at least 10 fold, at least 20 fold, at least 30 fold, at least 40 fold or at least 50 fold higher compared to the amount of secretion of effector cytokines such as IL-2, IFN-γ, TNF-α of the immune cell that is activated and stimulated solely by the antigen binding receptor, e.g. the CAR, and that is not boosted by the CCR.

For example, the number of killed target cells by the immune cell expressing both the antigen binding receptor, e.g. a CAR, and the CCR may be at least 1.5 fold, at least 2 fold, at least 5 fold, at least 10 fold, at least 20 fold, at least 30 fold, at least 40 fold or at least 50 fold higher compared to the number of killed target cells by the immune cell that is activated and stimulated solely by the antigen binding receptor, e.g. the CAR, and that is not boosted by the CCR.

The CCR is not able to mediate said immune response of the immune cell on its own, i.e. it is necessary for triggering said immune response that the immune cell expresses the CAR, the CCR merely boosts (assists) said immune response of said immune cell.

In contrast to a CAR, a CCR does not contain ITAM containing domains like CD3ζ or FcεRIγ and therefore no commonly known TCR-mediated signaling events including cis- and/or trans-activation may be induced upon CCR triggering.

The CCR can also render the immune cell less sensitive to tumor suppressive signals.

The CCR comprises an antigen binding domain, a transmembrane domain and cytoplasmic part comprising at least one co-stimulatory domain as described herein. Said at least one co-stimulatory domain of said CCR may be selected from the group consisting of ICOS, CD154, CD5, CD2, CD46, HVEM, CD8, CD97, TNFRSF18, CD30, SLAM, DAP10, CD64, CD16, CD89, MyD88, KIR-2DS, KIR-3DS, NKp30, NKp44, NKp46, NKG2D, ICAM, CD27, OX40, 4-1BB and CD28.

The CARs of the present invention may be designed to comprise any portion or part of the above-mentioned domains as described herein in any order and/or combination resulting in a functional CAR, i.e. a CAR that mediated an immune effector response of the immune effector cell that expresses the CAR.

The CCRs of the present invention may be designed to comprise any portion or part of the above-mentioned domains as described herein in any order and/or combination resulting in a functional CCR, i.e. a CRR that boosts the immune effector response of the immune effector cell that expresses the CAR and the CCR.

The terms "immune cell" or "immune effector cell" refer to a cell that may be part of the immune system and executes a particular effector function such as alpha-beta T cells, NK cells, NKT cells, B cells, innate lymphoid cells (ILC), cytokine induced killer (CIK) cells, lymphokine activated killer (LAK) cells, gamma-delta T cells, mesenchymal stem cells or mesenchymal stromal cells (MSC), monocytes or macrophages. Preferred immune cells are cells with cytotoxic effector function such as alpha-beta T cells, NK cells, NKT cells, ILC, CIK cells, LAK cells or gamma-delta T cells. Most preferred immune effector cells are T cells and NK cells. "Effector function" means a specialized function of a cell, e.g. in a T cell an effector function may be cytolytic activity or helper activity including the secretion of cytokines.

The term "tagged polypeptide" as used herein refers to a polypeptide that has bound thereto directly or indirectly at least one additional component, i.e. the tag. The polypeptide may be an antibody or antigen binding fragment thereof that binds to an antigen expressed on the surface of a target cell such as a tumor associated antigen on a cancer cell. The tag may be a hapten such as FITC, biotin, PE, or streptavidin and the hapten may be bound by the anti-hapten (anti-tag) binding domain of the CAR.

Haptens are small molecules that elicit an immune response only when attached to a large carrier such as a protein; the carrier may be one that also does not elicit an immune response by itself. Once the body has generated antibodies to a hapten-carrier adduct, the small-molecule hapten may also be able to bind to the antibody, but it will usually not initiate an immune response; usually only the hapten-carrier adduct can do this.

Alternatively, the "tagged polypeptide" may be a "target cell binding molecule" (TCBM) that is bound by an anti-linker/label epitope CAR (anti-LLE CAR) as disclosed in European patent application no. EP16196487.9. The adaptable CAR system of the TCBM and the anti-LLE CAR is briefly described in the following.

The anti-LLE CAR may comprise an extracellular binding domain capable of discriminating between a naturally occurring molecule in a subject and a target cell binding molecule (TCBM) comprising an antigen binding molecule (ABM), a label moiety (LaM) and a linker moiety (LiM), wherein said LiM conjugates said ABM and said LaM. The ABM is the polypeptide part of said tagged polypeptide. The label moiety (LaM) is a naturally occurring molecule in a subject or a derivative thereof. The linker moiety (LiM) is coupled to the label moiety (LaM). The LiM and LaM represent together the tag part of said tagged polypeptide. The anti-LLE chimeric antigen receptor binds TCBMs with LaM and a certain LiM with higher affinity than the endogenous label moiety without linker moiety. Thereby having an improved recognition/binding of TCBMs under physiological conditions where the endogenous LaM might be present.

The benefit of this approach is that the LaM that allows for an adaptable CAR system is non-immunogenic as it is a naturally occurring molecule endogenous to the subject. The LaM is a self-antigen, the LaM coupled to the LiM is a modified self-antigen, which build a novel epitope, the linker/label epitope (LLE), and the LLE is better bound by the LLE binding domain of the CAR than the natural occurring molecule in the subject.

Using a pure self-antigen as LaM bears a higher risk of an autoimmunity triggered by the immune cell expressing a CAR having an antigen binding domain against the LaM which is a self-antigen than using a modified self-antigen, the LLE. The risk of autoimmunity is reduced as the CAR binds with a lower preference, e.g. with a lower affinity, to the self-antigen than to the modified self-antigen.

The adaptable CAR still allows for efficient recruitment of the CAR immune cells to the TCBM that binds specifically to an antigen expressed on the surface of a target cell, e.g. a cancer cell. The naturally occurring molecule may be a molecule present in the circulatory system of a subject, but is bound at a lower affinity than the TCBM by the CAR as disclosed herein. Preferentially, the naturally occurring molecule in a subject may be an extracellular molecule or a molecule with partial extracellular structure, more preferentially, the naturally occurring molecule in a subject may be a human non-nuclear protein. This adaptable CAR improves efficacy of the therapy while minimizing the aforementioned risks of using immunogenic LaM/LiM.

The linker moiety and label moiety are part of the target cell binding molecule (TCBM) that also comprises an antigen binding moiety (ABM), wherein the linker moiety conjugates the LaM and the ABM. Generally, said ABM is directed against an antigen expressed on the surface of a target cell.

By administration of TCBM along with the CAR-expressing immune effector cells, the immune effector cell response can be targeted to only those cells expressing the antigen on the surface of the target cells, thereby reducing off-target toxicity. The CAR-expressing immune cells can be used as "universal" immune effector cells to target a wide variety of target cells, e.g. a wide variety of tumors without the need to prepare separate CAR constructs. The label/linker epitope of the TCBM recognized by the CAR may also remain constant. It is only the ABM of the TCBM that needs to be altered to allow the system to target target cells of different identity.

The anti-LLE CAR utilizes TCBMs as the bridge between immune effector cells expressing the CAR and target cells expressing the antigen. The TCBM comprises a label moiety (LaM) on one end of the molecule and an antigen binding moiety (ABM) on the other end, connected by a linker moiety. The sole requirement for the identity of the label moiety is only in that it must be a naturally occurring molecule in a subject (a self-antigen) and that the linker moiety conjugated variant thereof can be recognized and bound by a CAR expressed by an immune effector cell with higher affinity to the linker moiety conjugated variant thereof (the modified self-antigen) than to the non-linker moiety conjugated, naturally occurring variant.

Every molecule that might be capable of generating a LLE may be used as a linker moiety. The sole requirement for the identity of a linker moiety is that the linker moiety may be chemically conjugated (or coupled) to a label moiety or genetically (recombinantly) encoded and should be able to generate a new epitope at the context, the interface and/or environment of linker moiety and label moiety. The LiM may be preferentially a molecule that does not evoke or does not tend to evoke an immune reaction in the subject, e.g. the LiM is a self-antigen. In this case the interface of the LaM and LiM generates a novel epitope, the LLE.

The LiM may be e.g selected from the group consisting of peptides, proteins, nucleic acids, carbohydrates, polyhydroxyalkanoates, alkyl chains, alkanoic acids, carboxylic acids (e.g. ε-aminocaproic acid (6-aminohexanoic acid) or 6-(6-aminohexanamido)hexanoic acid) farnesyls, polyethylene glycols, lipids and derivatives thereof.

An especially preferred LiM may be a 6-(6-aminohexanamido) hexanoyl moiety, e.g. derived from 6-(6-aminohexanamido)hexanoic acid or 6-(6-aminohexanamido) hexanoic active ester, or a 6-aminohexanoyl moiety, e.g. derived from 6-aminohexanoic acid or 6-aminohexanoic active ester. The anti-LLE CAR may be a CAR, wherein said LaM is biotin and said LiM is a 6-(6-aminohexanamido) hexanoyl linker moiety or a 6-aminohexanoyl linker moiety.

The term "activates and stimulates an immune response of said immune effector cell" in the context of activation of the antigen binding receptor, e.g. the CAR means a primary induction of a signaling cascade which is associated with altered gene expression status in the immune effector cell initiating an immune response which includes, but is not limited to, proliferation, differentiation, cytokine release, cytolytic effector function and the like. For instance, MHC-dependent TCR-binding leads to TCR-clustering and the formation of an immunological synapse, which includes amongst others CD3, CD4, CD8. Subsequently, leading to binding of ZAP70 to CD3ζ that enables activation. Thereupon, several pathways are leading to the expression of ultimately T cell activating transcription factors like AP-1, NFAT and NF-κB that are required e.g. for an increased IL-2 production which enables proliferation and T cell mediated immune responses. However, to induce a persisting immune response, costimulatory receptors like CD28, CD27, CD137 (4-1BB) or ICOS have to become concomitantly activated. Any TCR-binding (Signal 1) without costimulatory signals (Signal 2) is associated with the inhibition of T cell effector function, this means T cells become anergic. The term "mediates an immune response of said immune effector cell" has the same meaning as "activates and stimulates an immune response of said immune effector cell" and may be used interchangeably. The term "boosts said immune response of said immune effector cell and/or ensures survival of said immune effector cell" in the context of activation of the CCR means an activation of a Signal-1-independent costimulatory signaling cascade in the immune effector cell providing intracellular conditions that promote survival and enable an enhanced Signal-1-dependent immune response. For instance, an immune effector cell co-expressing both a CAR and CCR can only be activated by the CAR comprising e.g. the activation domain CD3ζ, however, the cytolytic potential can be boosted by an additional triggering of costimulatory pathways (e.g. 4-1BB or CD28) via the CCR.

The term "antibody" as used herein is used in the broadest sense to cover the various forms of antibody structures including but not being limited to monoclonal and polyclonal antibodies (including full length antibodies), multispecific antibodies (e.g. bispecific antibodies), antibody fragments, i.e. antigen binding fragments of an antibody, immunoadhesins and antibody-immunoadhesin chimeras, that specifically recognize (i.e. bind) a target antigen. "Antibody fragments" comprise a portion of a full length antibody, preferably the variable domain thereof, or at least the antigen binding site thereof ("an antigen binding fragment of an antibody"). Examples of antibody fragments include Fab (fragment antigen binding), scFv (single chain fragment variable), single domain antibodies, diabodies, dsFv, Fab', diabodies, single-chain antibody molecules, and multispecific antibodies formed from antibody fragments.

As used herein, the term "antigen" is intended to include substances that bind to or evoke the production of one or more antibodies and may comprise, but is not limited to, proteins, peptides, polypeptides, oligopeptides, lipids, carbohydrates such as dextran, haptens and combinations thereof, for example a glycosylated protein or a glycolipid. The term "antigen" as used herein refers to a molecular entity that may be expressed on the surface of a target cell and that can be recognized by means of the adaptive immune system including but not restricted to antibodies or TCRs, or engineered molecules including but not restricted to endogenous or transgenic TCRs, CARs, scFvs or multimers thereof, Fab-fragments or multimers thereof, antibodies or multimers thereof, single chain antibodies or multimers thereof, or any other molecule that can execute binding to a structure with high affinity.

The term "further antigen" as used herein refers to the antigen which is bound by the antigen binding domain of the CCR. It might be the second antigen of the boosting system as disclosed herein if the antigen binding receptor directly binds to an antigen (the first antigen) expressed on the surface of a target cell. Alternatively, it might be the third antigen of the boosting system as disclosed herein if the antigen binding receptor binds a tag (the first antigen) of a tagged polypeptide, wherein the polypeptide binds to an antigen expressed on the surface of a target cell (second antigen). The term "said further antigen is not expressed on said target cell" means that the further antigen is either expressed on the surface of another cell that is not a cancer cell, preferentially it is a cell that is not in a disease state, or it is a freely circulating antigen in the circulatory system, e.g. soluble antigen, of a subject.

The terms "said further antigen is expressed on the surface of another cell than the target cell" and "said further antigen is expressed on the surface of a second target cell" may be used interchangeably. The second target cell that expresses an antigen recognized by the CCR may be a specific type of other cell (but another cell type than the (first) target cell) or may be any cell, e.g. in a subject that is treated with the immune effector cell as disclosed herein but not the (first) target cell (e.g. the cancer cell). The other cell than the target cell (or the second target cell) second target cell may be not in a disease state. A cell that is not in a disease state may be a cell that is not intended to be killed by the immune effector cell as disclosed herein, preferentially the cell that is not in a disease state is a healthy cell e.g. of a subject that is treated with the immune effector cell as disclosed herein.

The term "said further antigen is not expressed on a surface of a cell" as used herein means that the further antigen is not expressed an/or presented on the surface of a mammalian cell. If the further antigen is a non-polypeptide e.g. a polysaccharide such as dextran then the meaning is that the further antigen is not presented on the surface of a mammalian cell. The meaning of this term is that said further antigen is not a naturally occurring molecule to the surface of a mammalian cell.

The tumor associated antigen (TAA) as used herein refers to an antigenic substance produced in tumor cells. Tumor associated antigens are useful tumor or cancer markers in identifying tumor/cancer cells with diagnostic tests and are potential candidates for use in cancer therapy. Preferentially, the TAA may be expressed on the cell surface of the tumor/cancer cell, so that it may be recognized by the antigen binding receptor as disclosed herein.

The tumor associated antigen may be selected from the group consisting of CD33 (Sig1cc-3), CD123 (IL3RA), CD135 (FLT-3), CD44 (HCAM), CD44V6, CD47, CD184 (CXCR4), CLEC12A (CLL1), LeY, FRβ, MICA/B, CD305 (LAIR-1), CD366 (TIM-3), CD96 (TACTILE), CD133, CD56, CD29 (ITGB1), CD44 (HCAM), CD47 (IAP), CD66 (CEA), CD112 (Nectin2), CD117 (c-Kit), CD133, CD146 (MCAM), CD155 (PVR), CD171 (L1CAM), CD221 (IGF1), CD227 (MUC1), CD243 (MRD1), CD246 (ALK), CD271 (LNGFR), CD19, CD20, GD2, EGFR, and HMW-MAA (CSPG4). But there is no limitation to TAAs listed herein as the boosting system as disclosed herein may apply to any TAA expressed on a tumor or cancer cell.

The cluster of differentiation (abbreviated as CD) is a protocol used for the identification and investigation of cell surface molecules, regularly polypeptides, providing targets for immunophenotyping of cells.

The term "target cell" as used herein refers to cell which expresses an antigen on its cell surface that should be recognized (bound) by the antigen binding receptor as disclosed herein and/or by the CCR as disclosed herein.

The (first) target cell of the boosting system as disclosed herein may be a cell in a diseased state such a cancer cell expressing a tumor associated antigen that is directly or indirectly recognized by the antigen binding receptor as disclosed herein. The second target cell of the boosting system as disclosed herein may be a cell other than the first target cell. This second target cell may express an antigen on its surface that is directly or indirectly recognized by the CCR as disclosed herein.

The antigen receptors, e.g. the CARs and the CCRs as disclosed herein (polypeptide(s)), the nucleic acid molecule(s) encoding the CARs and/or the CCRs, recombinant expression vectors, cells expressing the CARs and the CCRs, and populations of cells expressing the CARs and the CCRs, can be isolated and/or purified. The term "isolated" means altered or removed from the natural state. For example, an isolated population of cells means an enrichment of such cells and separation from other cells which are normally associated in their naturally occurring state with said isolated cells. An isolated population of cells means a population of substantially purified cells which are a more homogenous population of cells than found in nature. Preferably the enriched cell population comprises at least about 90% of the selected cell type. In particular aspects, the cell population comprises at least about 90%, 91%, 92%, 93%, 94%, 95%, 96%, 97%, 98%, 99%, or even 100% of the selected cell type.

For example, a nucleic acid or a peptide naturally present in a living animal is not "isolated", but the same nucleic acid or peptide partially or completely separated from the coexisting materials of its natural state is "isolated". An isolated nucleic acid or protein can also exist in a non-native environment such as, for example, in a host cell.

Dextran is a complex branched glucan (polysaccharide made of many glucose molecules) composed of chains of varying lengths (from 3 to 2000 kilodaltons). Dextran of any length, e.g. from 3 to 2000 kDa may be used for the herein disclosed applications. Preferentially the dextran used may be over 5, 10, 20, 100 or 200 kDa. In some embodiments of the invention, the dextran used may be a dextran from 60 to 200 kDa. The soluble dextran as used herein may present many antigens for the CCR that binds to dextran as disclosed herein. The dextran may be a poly-antigen instead of a mono-antigen for the anti-dextran CCR.

Said dextran may be unbound dextran, i.e. free dextran, soluble dextran or dextran conjugated to colloidal nano- or microparticles. Said dextran may be administered to a patient in need thereof that harbours the immune effector cell as disclosed herein to boost said immune effector cell under controllable conditions. Alternatively, said dextran may be coupled to an antibody or antigen binding fragment thereof, wherein said antibody may bind specifically to another antigen that may be expressed on said target cell or on said other cell.

As used herein, the term "subject" refers to a mammal such as mouse, rat, cow, pig, goat, chicken dog, monkey or human. Preferentially, the subject is a human. The subject may be a subject suffering from a disorder such as cancer (a patient), but the subject may be also a healthy subject.

The term "autologous" as used herein refers to any material derived from the same subject to who it is later re-introduced.

The term "allogeneic" as used herein refers to any material derived from a different subject of the same species as the subject to who the material is re-introduced.

The terms "therapeutically effective amount" or "therapeutically effective population" mean an amount of a cell population which provides a therapeutic benefit in a subject.

The terms "specifically binds" or "specific for" with respect to an antigen binding domain of an antibody, of an antigen binding fragment thereof, as used e.g. in the CAR and CCR as disclosed herein, or in the tagged polypeptide, e.g. the TCBM refer to an antigen binding domain which recognizes and binds to a specific antigen, but does not substantially recognize or bind other molecules in a sample. An antigen binding domain that binds specifically to an antigen from one species may bind also to that antigen from another species. This cross-species reactivity is typical to many antibodies and therefore not contrary to the definition of that antigen binding domain as specific. An antigen binding domain that specifically binds to an antigen may bind also to different allelic forms of the antigen (allelic variants, splice variants, isoforms etc.) or homologous variants of this antigen from the same gene family. This cross reactivity is typical to many antibodies and therefore not contrary to the definition of that antigen binding domain as specific.

The terms "engineered cell" and "genetically modified cell" as used herein can be used interchangeably. The terms mean containing and/or expressing a foreign gene or nucleic acid sequence which in turn modifies the genotype and/or phenotype of the cell or its progeny. Especially, the terms refer to the fact that cells, preferentially immune cells can be manipulated by recombinant methods well known in the art to express stably or transiently peptides or proteins which are not expressed in these cells in the natural state. For example, immune cells are engineered to express an artificial construct such as a chimeric antigen receptor on their cell surface.

The term "disorder" means a functional abnormality or disturbance in a subject such as a cancer, an autoimmune disorder, or an infection by virus, bacteria, parasite, or others.

The term "treat" (treatment of) a disorder (e.g. cancer) as used herein means to reduce the frequency or severity of at least one sign or symptom of a disease or disorder experienced by a subject.

The term "expression" as used herein is defined as the transcription and/or translation of a particular nucleotide sequence driven by its promoter in a cell.

The term "epitope" means the part of an antigen that may be recognized by the immune system, specifically by antibodies, B cells, or T cells. For example, the epitope is the specific piece of the antigen to which an antibody or antigen binding fragment thereof binds.

The terms "linker/label epitope" (LLE) or "label/linker epitope" as used herein can be used interchangeably and refer to an epitope formed by the context, the interface and/or environment of conjugated linker moiety and label moiety of the TCBM as disclosed herein.

The epitope generated by the coupling of the label moiety with a linker moiety does not occur naturally in a subject. The generated epitope comprises a part of said LaM and a part of said LiM. Preferentially, the LLE does not evoke or does not tend to evoke an immune reaction in a subject intended to be treated with cells expressing the anti-LLE CAR as disclosed herein. The only requirement for the LLE is that it is an epitope with regard to the CAR comprising the LLE binding domain. An extracellular LLE binding domain of a CAR as disclosed herein that is derived from an epitope recognizing molecule such as an antibody that recognizes the label/linker epitope binds with a higher preference to the newly created epitope, i.e. the label/linker epitope (the modified self-antigen), than to the endogenous label moiety without linker moiety, i.e. the naturally occurring molecule in the subject (the self-antigen).

Said extracellular LLE binding domain of the anti-LLE CAR binds with an at least twofold, preferentially at least 5-fold, more preferentially at least 10-fold higher affinity to said LLE than to the said naturally occurring molecule.

The amino acid sequences of SEQ ID NO: 1 to SEQ ID NO: 23 as given in the sequence listing protocol are mostly partial or full sequences of CARs as disclosed herein. Said sequences of SEQ ID NO: 1 to SEQ ID NO: 23 may also comprise variants of these sequences, respectively, which have some amino acids deleted, added or replaced while still retaining the intended function as described herein. Therefore, included in this definition are variants of the amino acid sequences in SEQ ID NO: 1 to SEQ ID NO: 23, respectively, such as amino acid sequences essentially similar to SEQ ID NO: 1 to SEQ ID NO: 23, respectively, having a sequence identity of at least 70%, or at least 75%, 80%, 85%, 90%, 95%, 97%, 98% or 99% at the amino acid sequence level. In general, all amino acid variations which do not lead to intentional changes of the intended function of the sequences SEQ ID NO: 1 to SEQ ID NO: 23, respectively, are included under this definition. In the context of the present invention, "sequence identity" may be determined using pairwise alignments using alignments programs for amino acid sequences well known to the art.

The "circulatory system" is an organ system of a subject that permits blood to circulate and transport nutrients (such as amino acids and electrolytes), oxygen, carbon dioxide, hormones, and blood cells to and from the cells in the body to provide nourishment and help in fighting diseases, stabilize temperature and pH, and maintain homeostasis. The circulatory system comprises two separate systems: the cardiovascular system, which distributes blood, and the lymphatic system, which circulates lymph.

The term "naturally occurring molecule in a subject or a derivate thereof" as used herein refers to molecules or substances in a subject, preferably said molecules are located extracellularly or have at least an extracellular part, e.g. a transmembrane spanning protein. The naturally occurring molecule may exist in free form or covalently or non-covalently bound to another molecule, e.g. bound to a protein. For example, biotin exists in free form circulating in the blood system, but also bound to e.g. plasmaprotein.

Due to this requirement these molecules are non-immunogenic as they are endogenous molecules (self-antigens) of the subject. As an example, biotin is a naturally occurring molecule in a subject as it is a circulatory molecule in the blood system (circulatory system) of a subject. The term "derivative thereof" means in this context that said naturally occurring molecule in a subject may undergo some minor modifications without changing the nature of said molecule. Said modifications are not identical with the conjugation of the linker moiety to said molecule. The term "tumor" is known medically as a neoplasm. Not all tumors are cancerous; benign tumors do not invade neighboring tissues and do not spread throughout the body.

The term "cancer" is known medically as a malignant neoplasm. Cancer is a broad group of diseases involving unregulated cell growth and includes all kinds of leukemia. In cancer, cells (cancerous cells) divide and grow uncontrollably, forming malignant tumors, and invading nearby parts of the body. The cancer may also spread to more distant parts of the body through the lymphatic system or bloodstream. There are over 200 different known cancers that affect humans.

The terms "automated method" or "automated process" as used herein refer to any process being automated through the use of devices and/or computers and computer software which otherwise would or could be performed manually by an operator. Methods (processes) that have been automated require less human intervention and less human time to deliver. In some instances a method is automated if at least one step of the method is performed without any human support or intervention. Preferentially the method is automated if all steps of the method are performed without human support or intervention.

This invention is further illustrated by the following examples, which are not to be construed in any way as imposing limitations upon the scope thereof.

EXAMPLES

Figure 3:
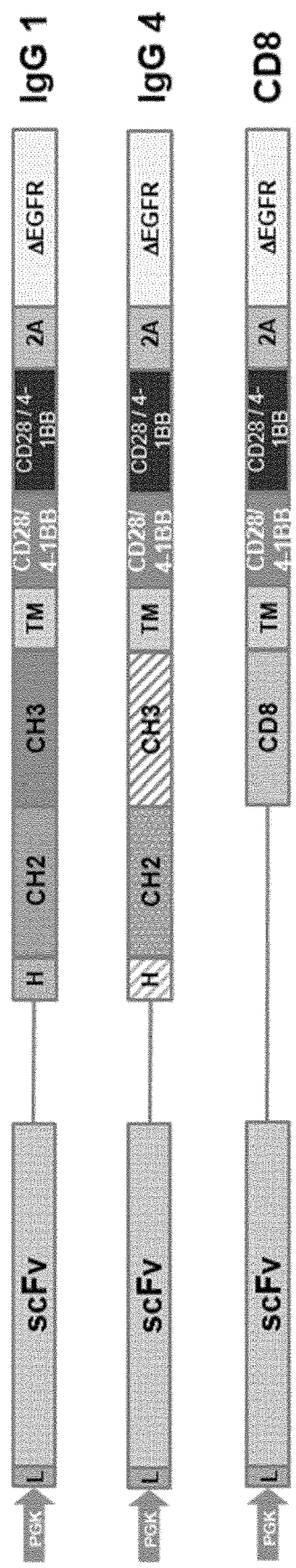
FIG. 3: Schematic representation of the different anti-CD20 CCR formats. The leader sequence "L" is derived from human CD8 (SEQ ID NO: 1), scFv is derived from SEQ ID NO: 13, hinge and spacers "H" and "CH2", "CH3" and "CD8" are derived from human IgG4 (SEQ ID NO: 5), human CD8 (SEQ ID NO: 8) or human IgG1 (SEQ ID NO: 14). The transmembrane domain "TM" is from human CD8 (SEQ ID NO: 9), while co-stimulatory domains are from 4-1 BB (SEQ ID NO: 10) and/or CD28 (SEQ ID NO: 16). All CCRs are expressed together with the marker gene ΔEGFR linked by a 2A element (SEQ ID NO: 15).

Example 1. Generation of Anti-HMW-MAA CAR and Anti-CD20 CCR Co-Expressing T Cells 1.1 Construct Design In order to develop CAR/CCR T cells recognizing both, HMW-MAA as well as CD20, different CAR and CCR encoding lentiviral constructs were designed. The anti-HMW-MAA CAR comprises either a human CD8 leader sequence (SEQ ID NO: 1) or a murine leader sequence (SEQ ID NO: 2) followed by a scFv derived from the murine monoclonal antibodies (mAB) 225.28s in VL-VH orientation (SEQ ID NO: 3) or 763.74 in VH-VL orientation (SEQ ID NO: 4), linked by a flexible $(G_4S)_3$ linker, respectively. These scFvs were subcloned into lentiviral transfer vector plasmids containing different extracellular spacer variants based on human IgG4 (HC) (SEQ ID NO: 5-7) or CD8 (SEQ ID NO: 8), a human CD8 transmembrane domain (SEQ ID NO: 9), a intracellular human 4-1BB costimulation domain (SEQ ID NO: 10) linked to a human CD3ζ signaling domain (SEQ ID NO:11) as well as a 2A element-linked surface marker (ΔLNGFR) (SEQ ID NO: 12) (FIG. 2). The anti-CD20 CCR encoding lentiviral constructs were generated by subcloning the human CD8 leader sequence (SEQ ID NO: 1) in combination with a scFv derived from the murine mAB Leu16 in VL-VH orientation (SEQ ID NO: 13), linked by a $(G_4S)_3$ linker, into lentiviral transfer vector plasmids containing either extracellular spacer variants derived from human IgG1 (SEQ ID NO: 14), human IgG4 (SEQ ID NO: 5) or human CD8 stalk (SEQ ID NO: 8). All anti-CD20 CCR encoding constructs contain the same human CD8 transmembrane domain (SEQ ID NO: 9) as well as the C-terminally placed, 2A element-linked ΔEGFR (SEQ ID NO: 15) as surface marker, but differ with regard to the costimulation domains that can either be 4-1BB (SEQ ID NO: 10), CD28 (SEQ ID NO: 16) or combinations thereof (FIG. 3).

Any version of both CAR encoding constructs can also be linked via a 2A element followed by a C-terminally placed ΔLNGFR in the lentiviral backbone to generate double constructs (DC).

1.2 Generation of LV Particles

For production of lentiviral particles $0.5 \times 10^5/cm^2$ HEK293T cells were seeded in a T175 cell culture flask (175 $cm^2$) using 25 mL medium (DMEM, 10% (v/v) FCS, 2 mM L-glutamine) and incubated overnight at 37° C., 5% $CO_2$. On the next day the adherent cells typically showed 75-90% confluency. Medium was exchanged to DMEM with 2 mM L-glutamine, without FCS and transfection DNA mixes were prepared (using Lipofectamine 3000, ThermoFisher reagent protocol). For this a total DNA amount of 0.2 µg/cm² (35 µg for one T175 flask) was used and two separate mixes A (DNA) and B (Lipofectamine) were prepared. For Mix A: Transfer-vector-plasmid 0.073 µg/cm² (12.7 µg), helper-plasmid 1 (VSVg) 0.018 µg/cm² (3.18 µg), helper plasmid 2 (gag/rev/pol) 0.109 µg/cm² (19.09 µg), P3000 enhancer reagent 2 µg/µg total DNA, and Opti-MEM 0.033 mL/cm² were mixed by brief vortexing. For Mix B: Lipofectamine 3000 0.75 µ/cm² was resuspended in Opti-MEM 0.033 mL/cm². Mix A and B were incubated separately for 5 minutes, then mix A and B were mixed together gently, and incubated 20 minutes at RT. Then the lipid/DNA complexes were added dropwise to plated cells and incubated at 37° C. for approximately 12 hours. After this, the medium was replaced with 0.133 mL/cm² fresh medium (DMEM, 10% FCS, 2 mM L-glutamine) and incubated at 37° C., 5% $CO_2$ for 24 hours. Assembled lentiviral particles were harvested by carefully removing the cell culture supernatant by pipetting. Cellular debris was removed from the supernatant by centrifugation for 10 min at 5000×g. The LV-containing supernatant was then directly used for transduction of T cells, stored overnight at 4° C. or snap frozen in liquid nitrogen and stored at −80° C. For a second round of lentiviral particle production 0.133 mL/cm² fresh medium (DMEM, 10% FCS, 2 mM L-glutamine) was added to the transfected HEK293T cells and incubation was continued for another 24 h at 37° C., 5% $CO_2$. After 24 h the supernatant was harvested as described previously.

1.3 Transduction, Expansion, Enrichment and Expression Analysis of Anti-HMW-MAA CAR and Anti-CD20 CCR Co-Expressing T Cells Blood samples were drawn from healthy donors and PBMCs were generated by separation on Pancoll (PAN-Biotech). PAN T cells were selected using MACS technology (Miltenyi Biotec). For T cell activation and -expansion the T cell activation/expansion kit, human (Miltenyi Biotec) was used according to the manufacturer's instructions. T cells were seeded into 24-well plates with 2 mL T cell suspension per well at a concentration of $1 \times 10^6$ cells/mL in TexMACS medium containing human AB serum (10% (v/v) GemCell), IL-7 (6.25 ng/mL) and IL-15 (12.5 ng/mL) (Miltenyi Biotec).

Figure 4:
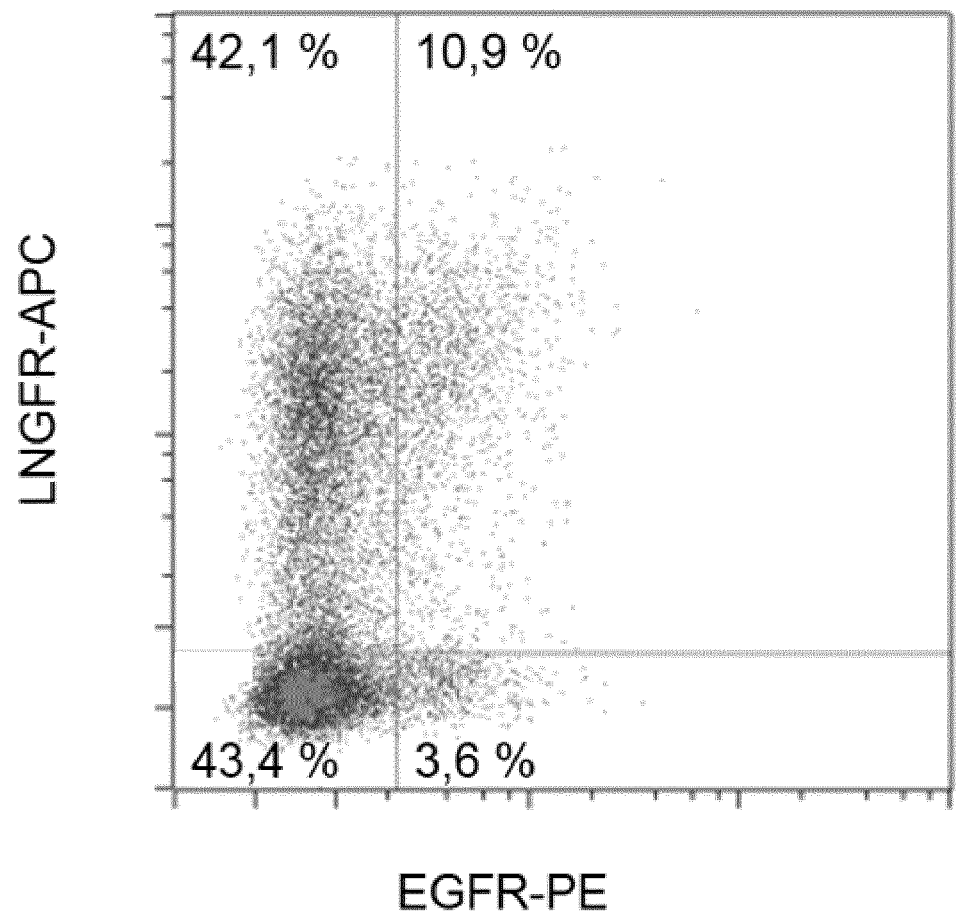
FIG. 4: Exemplary transgenic expression of ΔLNGFR and ΔEGFR of primary T cells after lentiviral co-transduction with an anti-HMW-MAA CAR and an anti-CD20 CCR on day 6 after activation. A frequency of 10.9% expressed both surface markers.
Figure 5:
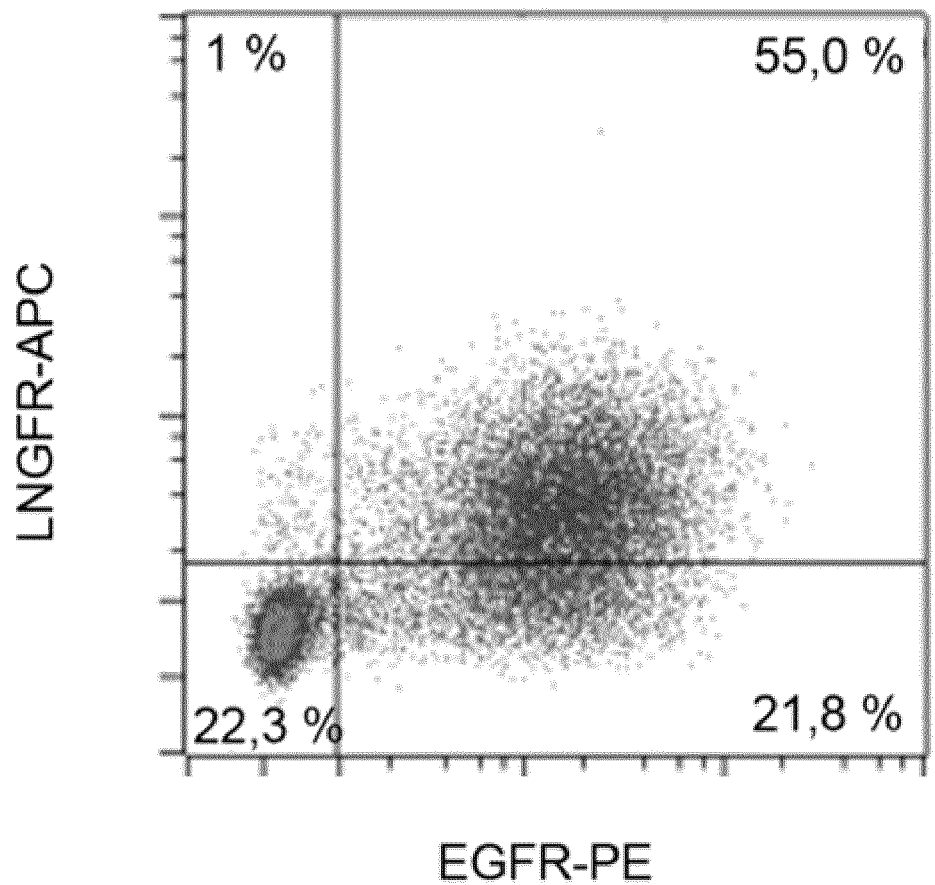
FIG. 5: Exemplary transgenic expression of ΔLNGFR and ΔEGFR of primary T cells (day 16) after an enrichment of co-transduced T cells on day 7. The frequency of ΔLNGFR and ΔEGFR co-expressing T cells could be increased from 10.9% to 55.0%.

Transduction/co-transduction with either LV_anti-HMW-MAA CAR in combination with LV_anti-CD20 CCR or both separately was performed on day 2 after activation. On day 6 after activation, transduction efficiency was measured by flow analysis using anti-LNGFR APC (Miltenyi Biotec) and anti-EGFR-PE (BD) (FIG. 4). The next day, ΔLNGFR/EGFR-expressing cells were separated by using the anti-Biotin MultiSort Kit (Miltenyi Biotec) with anti-ΔLNGFR-Biotin/anti-Biotin Microbeads and anti-EGFR-PE/anti-PE Microbeads (Miltenyi Biotec) according to the manufacturer's instructions, respectively. Enriched cells were reactivated using the T cell activation/expansion kit, human (Miltenyi Biotec) and seeded in a 24-well plate at a concentration of $1 \times 10^6$ cells/mL (2 mL per well). Cells were then continuously expanded and transduction efficiency was determined again on day 16 after their first activation by flow analysis (FIG. 5).

Example 2. Generation of Target Cell Lines for Cytotoxicity Analysis 2.1 Generation of Stably Transduced Luciferase Expressing Cell Lines A lentiviral transfer vector plasmid was generated encoding for a Firefly luciferase gene and a 2A element-linked GFP sequence as well known in the art. LV particles were generated as already described under 1.2. Tumor cell transduction was similar to that for T cells described under 1.3. After transduction, tumor cells were upscaled and transduction efficiency was evaluated by flow cytometry (GFP excitation 488 nm laser, band pass filter 525/50 nm). Subsequently, a single-cell expansion was performed according to protocols known by skilled persons. GFP-expressing subclones were upscaled again, cryopreserved and used for functional analyses. In doing so, the following cell lines were generated: $Mel526^{Luciferase\_eGFP}$, $JeKo-1^{Luciferase\_eGFP}$, $Raji^{Luciferase\_eGFP}$ and $NALM6^{Luciferase\_eGFP}$.

2.2 Generation of Stably Transduced Luciferase and CD20 Co-Expressing Cell Lines Due to the lack of HMW-MAA-expressing and CD20-co-expressing cell lines, $Mel526^{Luciferase\_eGFP}$ were further modified using a lentiviral construct encoding for human CD20 gene according to the description in 2.1. The newly generated cell line $Mel526^{Luciferase\_eGFP\_CD20}$ stably expressed Luciferase, eGFP and CD20 as detected by flow cytometry using anti-CD20 APC (Miltenyi Biotec).

Figure 6A:
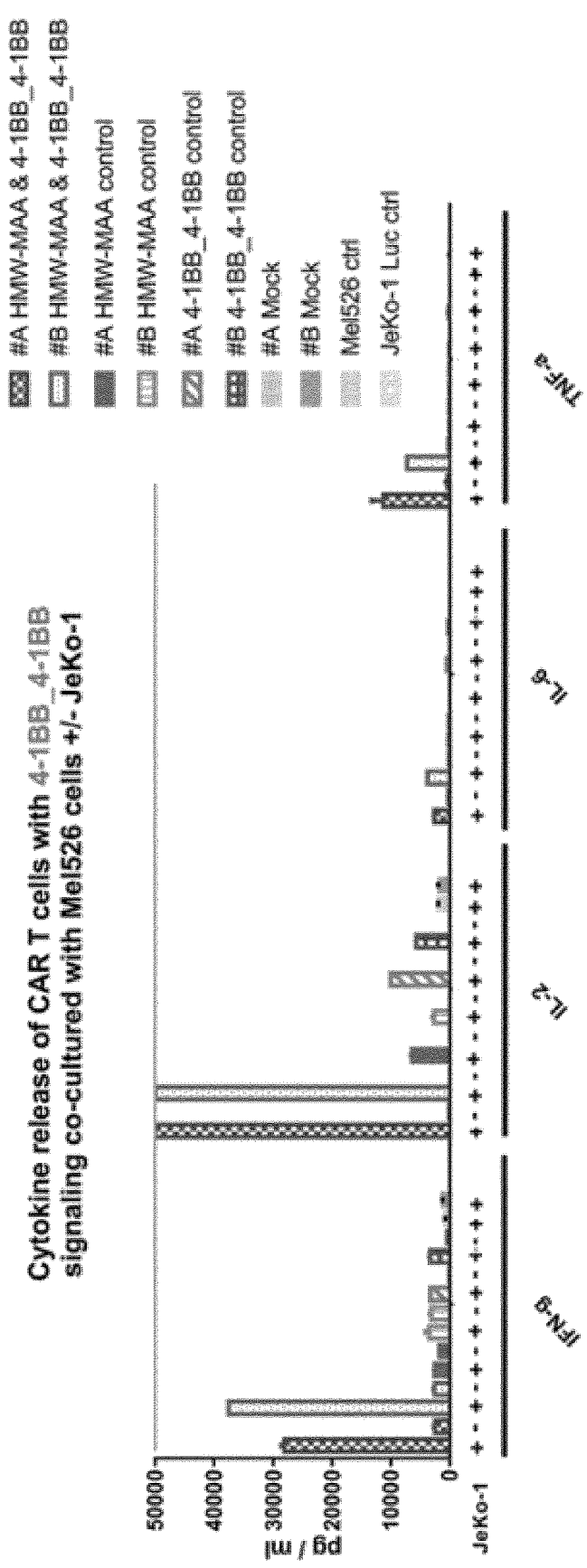
FIG. 6: a) Data on IFN-γ, IL-2, IL-6 and TNF-α production of anti-HMW-MAA CAR and anti-CD20 CCR (4-1BB_4-1BB signaling) co-expressing T cells, non-transduced T cells (Mock) as well as anti-HMW-MAA CAR or anti-CD20 CCR transduced T cells (control) after co-culturing with Mel526 cells (HMW-MAA+) in the presence or absence of JeKo-1 cells (CD20+) for 24 h. 2 biological replicates; n=2; 50000 pg/ml was the MACSplex detection limit. b) Data on IFN-γ, IL-2, IL-6 and TNF-α production of anti-HMW-MAA CAR and anti-CD20 CCR (4-1BB signaling) co-expressing T cells, non-transduced T cells (Mock) as well as anti-HMW-MAA CAR or anti-CD20 CCR transduced T cells (control) after co-culturing them with Mel526 cells (HMW-MAA+) in the presence or absence of JeKo-1 cells (CD20+) for 24 h. 2 biological replicates; n=2; 50000 pg/ml was the MACSplex detection limit. c) Data on IFN-γ, IL-2, IL-6 and TNF-α production of anti-HMW-MAA CAR and anti-CD20 CCR (CD28_CD28 signaling) co-expressing T cells, non-transduced T cells (Mock) as well as anti-HMW-MAA CAR or anti-CD20 CCR transduced T cells (control) after co-culturing them with Mel526 cells (HMW-MAA+) in the presence or absence of JeKo-1 cells (CD20+) for 24 h. 2 biological replicates; n=2; 50000 pg/ml was the MACSplex detection limit. d) Data on IFN-γ, IL-2, IL-6 and TNF-α production of anti-HMW-MAA CAR and anti-CD20 CCR (CD28 signaling) co-expressing T cells, non-transduced T cells (Mock) as well as anti-HMW-MAA CAR or anti-CD20 CCR transduced T cells (control) after co-culturing them with Mel526 cells (HMW-MAA+) in the presence or absence of JeKo-1 cells (CD20+) for 24 h. 2 biological replicates; n=2; 50000 pg/ml was the MACSplex detection limit. e) Data on IFN-γ, IL-2, IL-6 and TNF-α production of anti-HMW-MAA CAR and anti-CD20 CCR (CD28_4-1BB signaling) co-expressing T cells, non-transduced T cells (Mock) as well as anti-HMW-MAA CAR or anti-CD20 CCR transduced T cells (control) after co-culturing them with Mel526 cells (HMW-MAA+) in the presence or absence of JeKo-1 cells (CD20+) for 24 h. 2 biological replicates; n=2; 50000 pg/ml was the MACSplex detection limit.
Figure 6B:
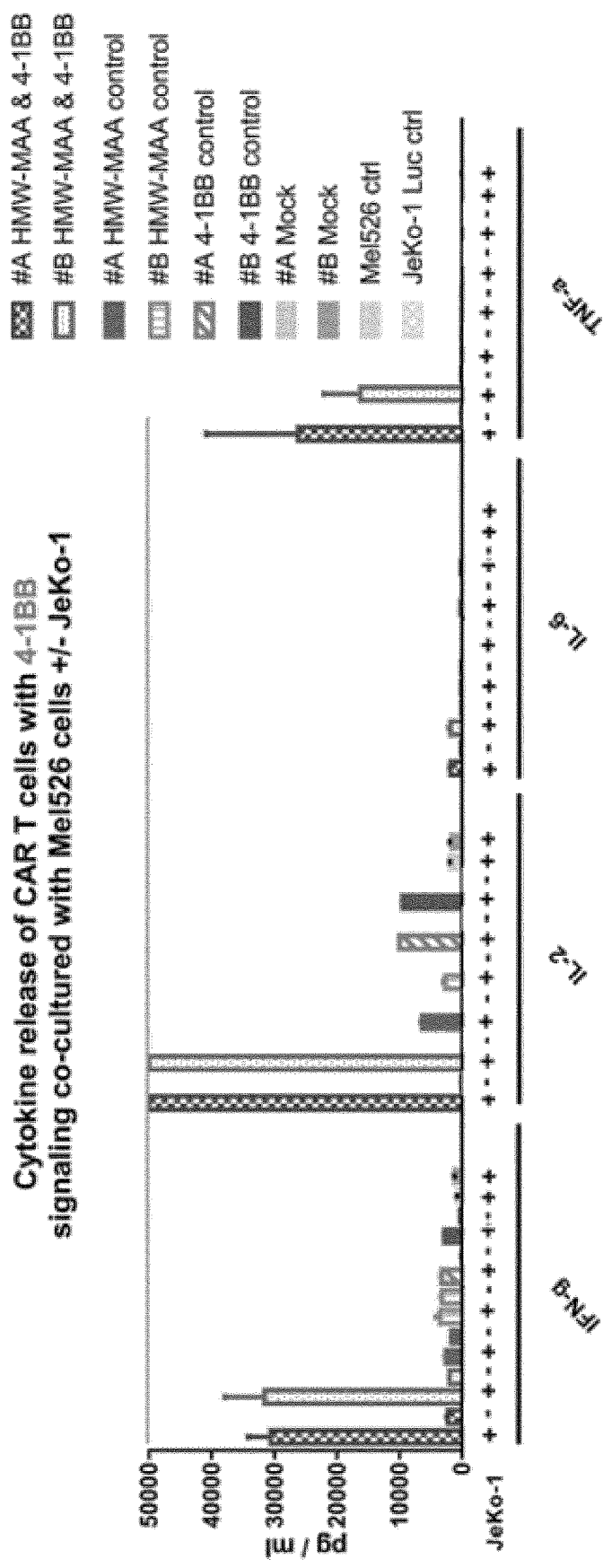
Figure 6:
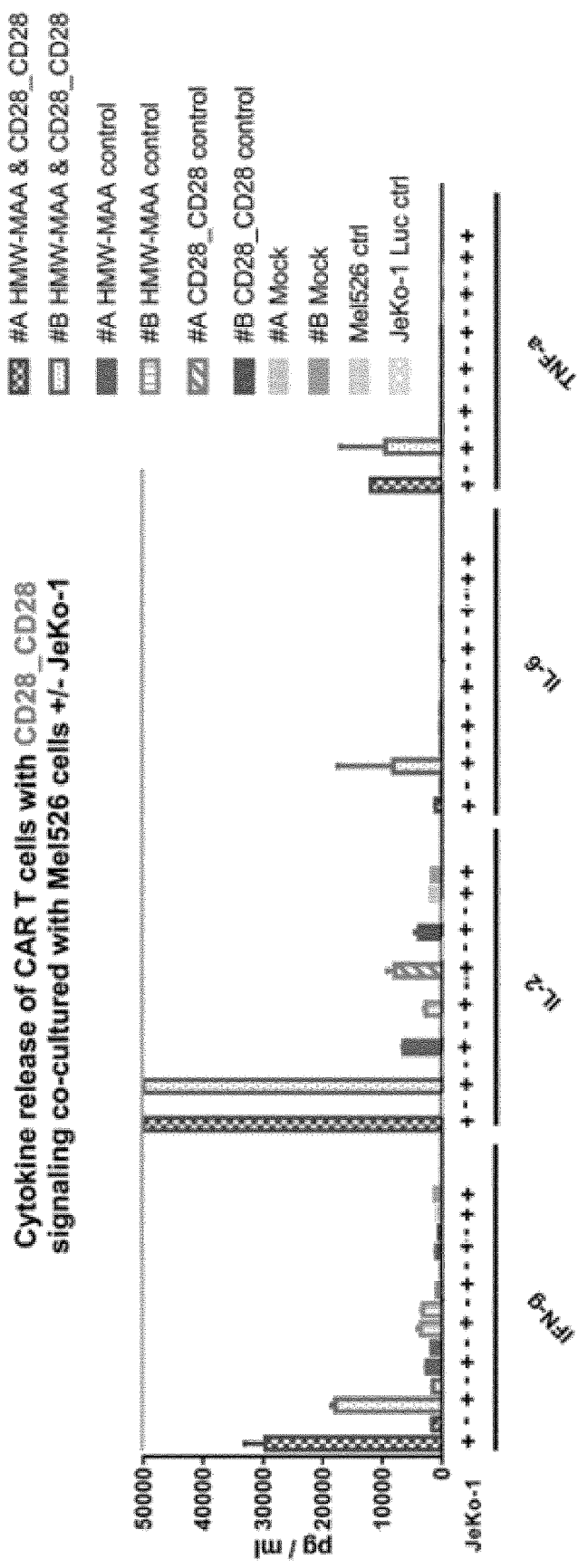
Figure 6:
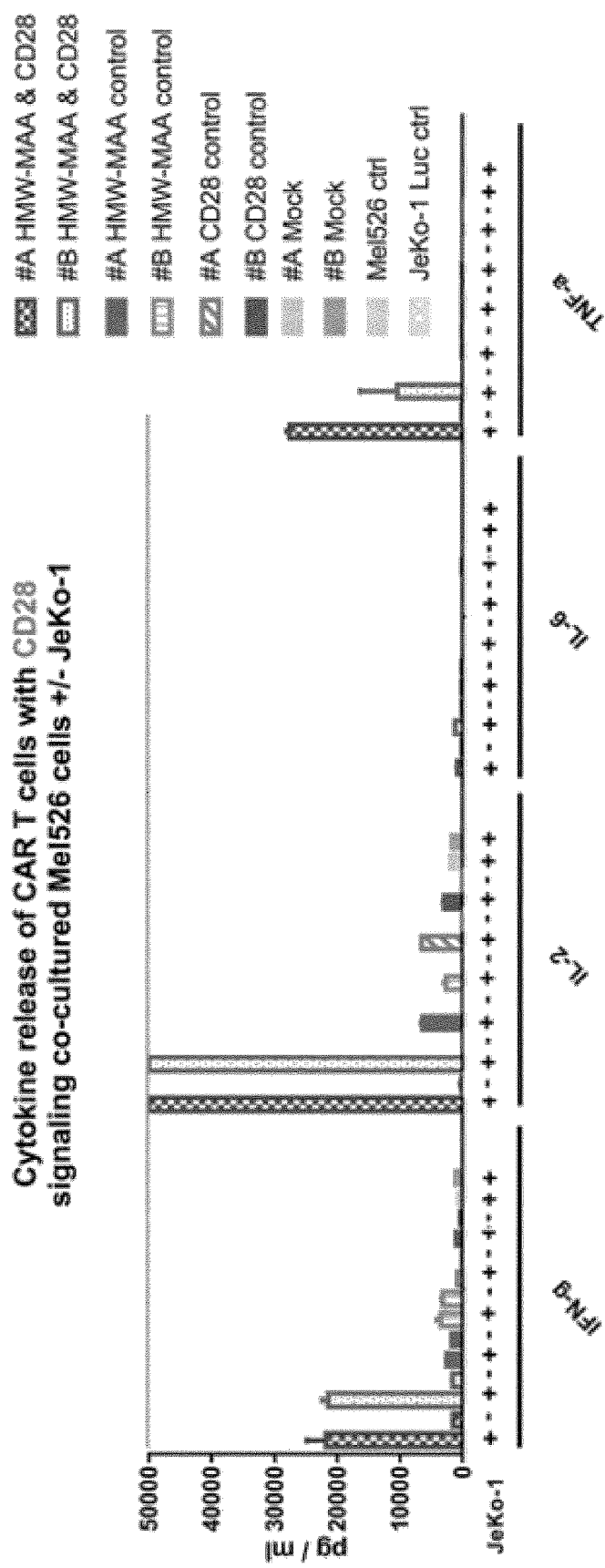
Figure 6E:
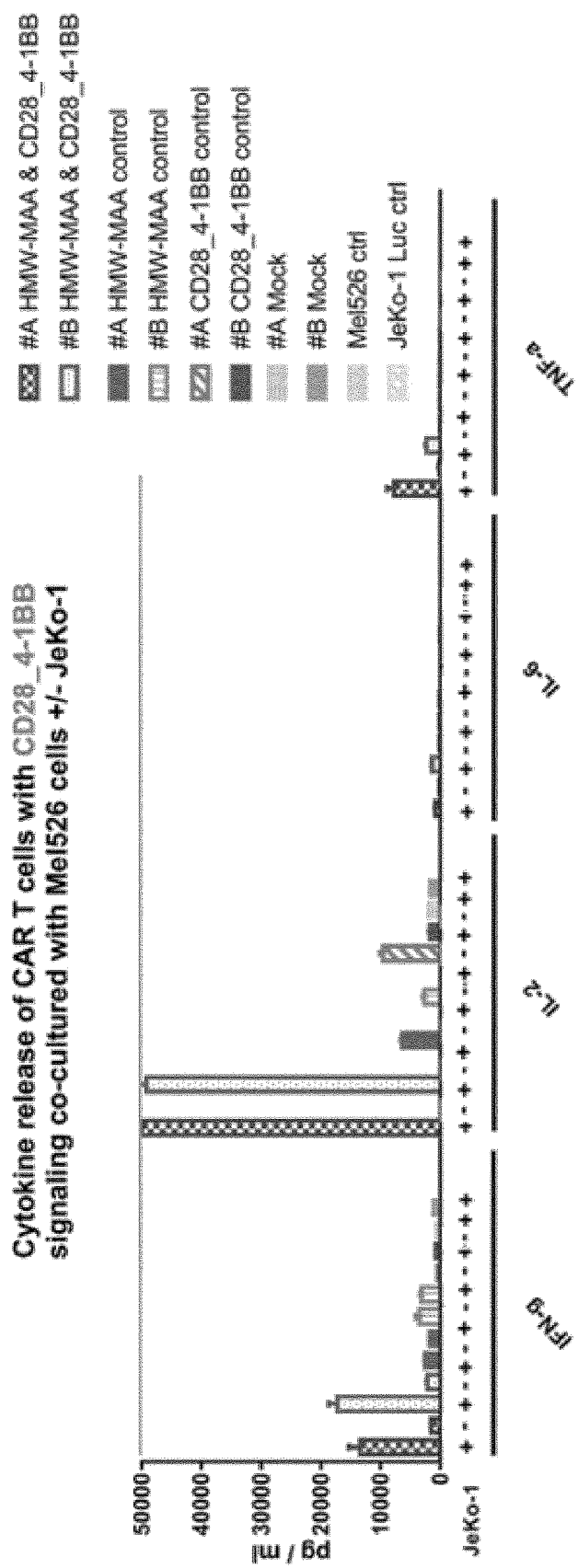

Example 3. Functionality Testing Via Cytokine Release and Killing Assay 3.1 Analyzing the Functionality in Trans Via a Cytokine-Release Assay On day 16 after activation, 1E5 CAR/CCR T cells were co-cultured in a total volume of 200 µl TexMACS Medium (Miltenyi Biotec) in a 96-well plate with 2E4 HMW-MAA-expressing Mel526 cells in the presence or absence of 1E5 CD20-expressing cells (e.g. autologous B cells, JeKo-1 or Raji) for 24 h. Subsequently, cytokine release in the supernatant was measured using the MACSPlex Cytokine 12 Kit, human (Miltenyi Biotec) according to the manufacturer's instructions (FIG. 6).

3.2 Analyzing the Functionality in Cis Via a Cytokine-Release Assay

Figure 7A:
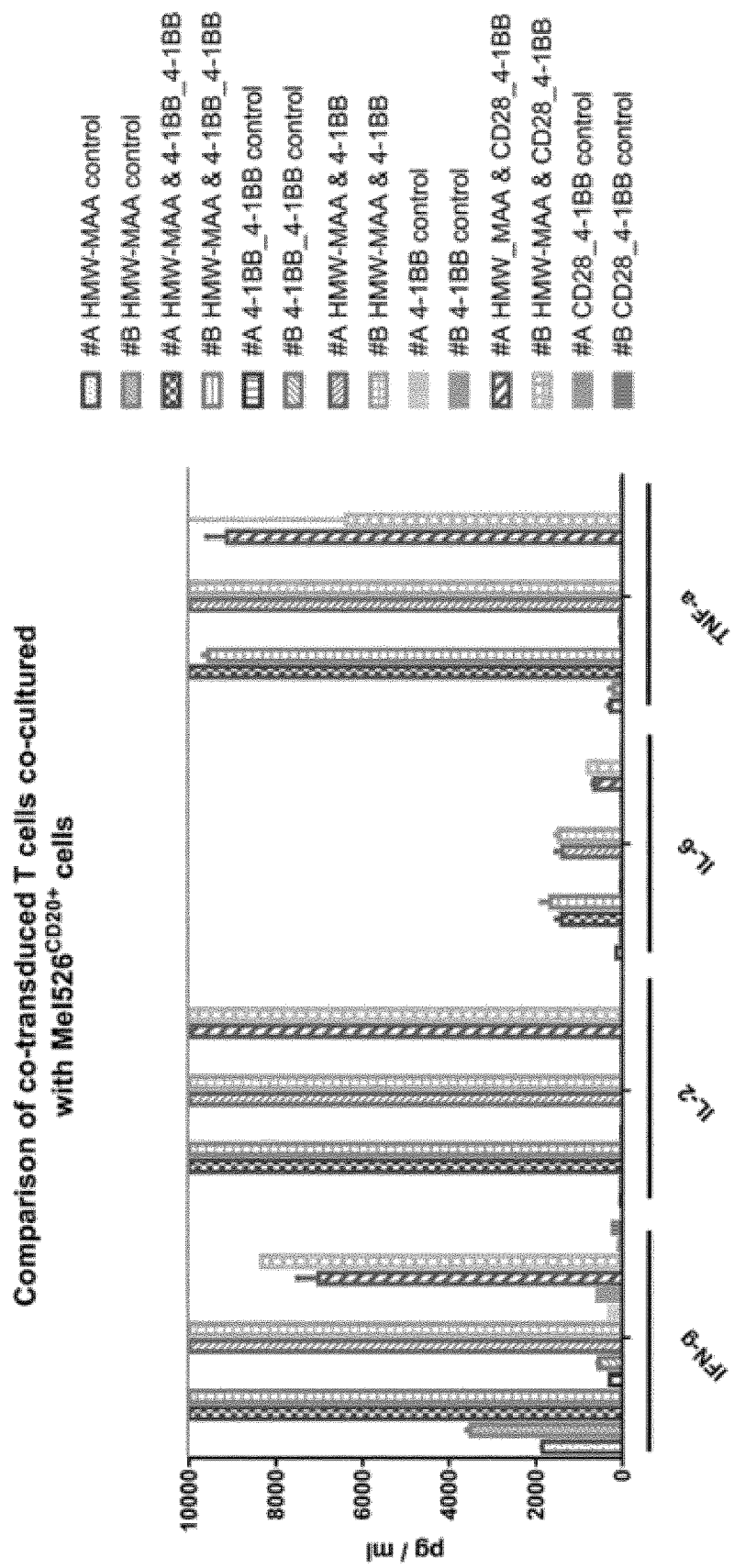
FIG. 7: a) Data on IFN-γ, IL-2, IL-6 and TNF-α production of anti-HMW-MAA CAR and anti-CD20 CCR (with either 4-1BB_4-1BB signaling, 4-1BB signaling or CD28_4-1BB signaling) co-expressing T cells as well as anti-HMW-MAA CAR or anti-CD20 CCR transduced T cells (control) after co-culturing them with transgenic Mel526 cells (HMW-MAA+ and CD20+) for 24 h. 2 biological replicates; n=2; 10000 pg/ml was the MACSplex detection limit. b) Data on IFN-γ, IL-2, IL-6 and TNF-α production of anti-HMW-MAA CAR and anti-CD20 CCR (with either CD28_CD28 signaling or CD28 signaling) co-expressing T cells as well as anti-HMW-MAA CAR or anti-CD20 CCR transduced T cells (control) after co-culturing them with transgenic Mel526 cells (HMW-MAA+ and CD20+) for 24 h. 2 biological replicates; n=2; 10000 pg/ml was the MACSplex detection limit.
Figure 7B:
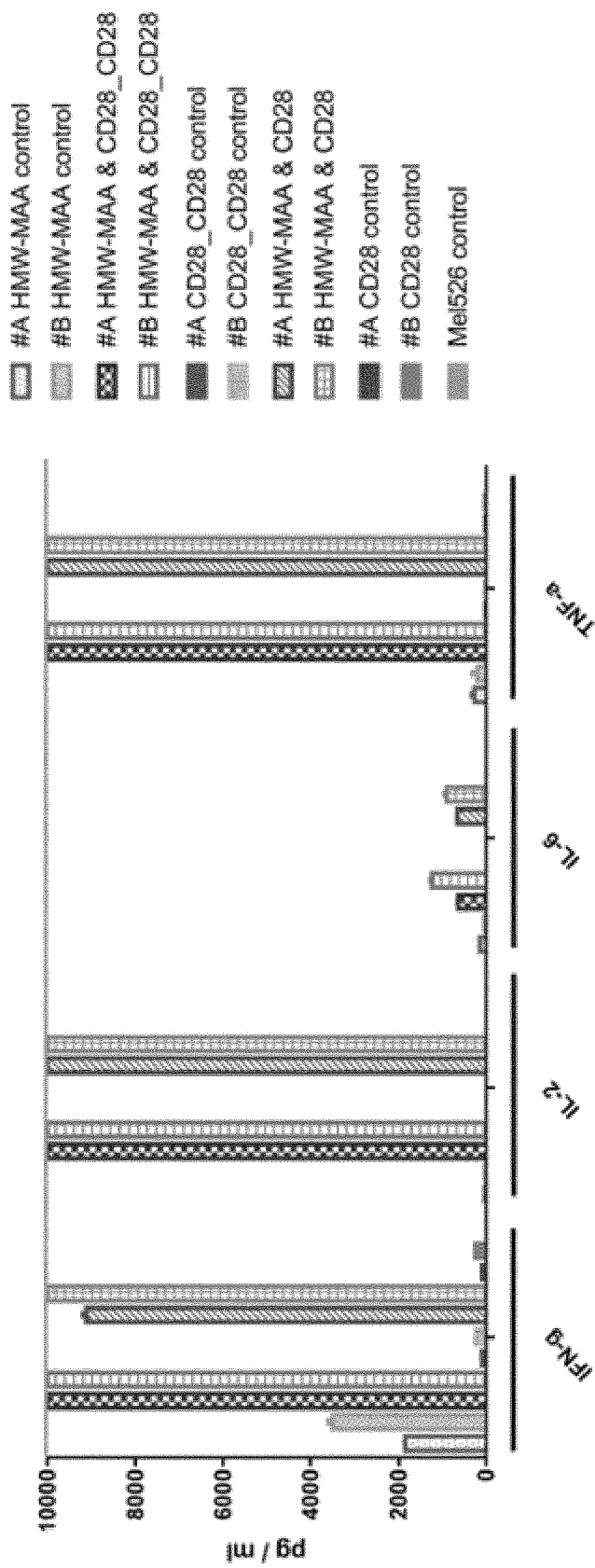

According to 3.1, 1E5 CAR/CCR T cells were co-cultured with 2E4 $Mel526^{Luciferase\_eGFP\_CD20}$ cells for 24 h, before the released cytokines were quantified using the MACSPlex Cytokine 12 Kit, human (Miltenyi Biotec) according to the manufacturer's instructions (FIG. 7).

Figure 8:
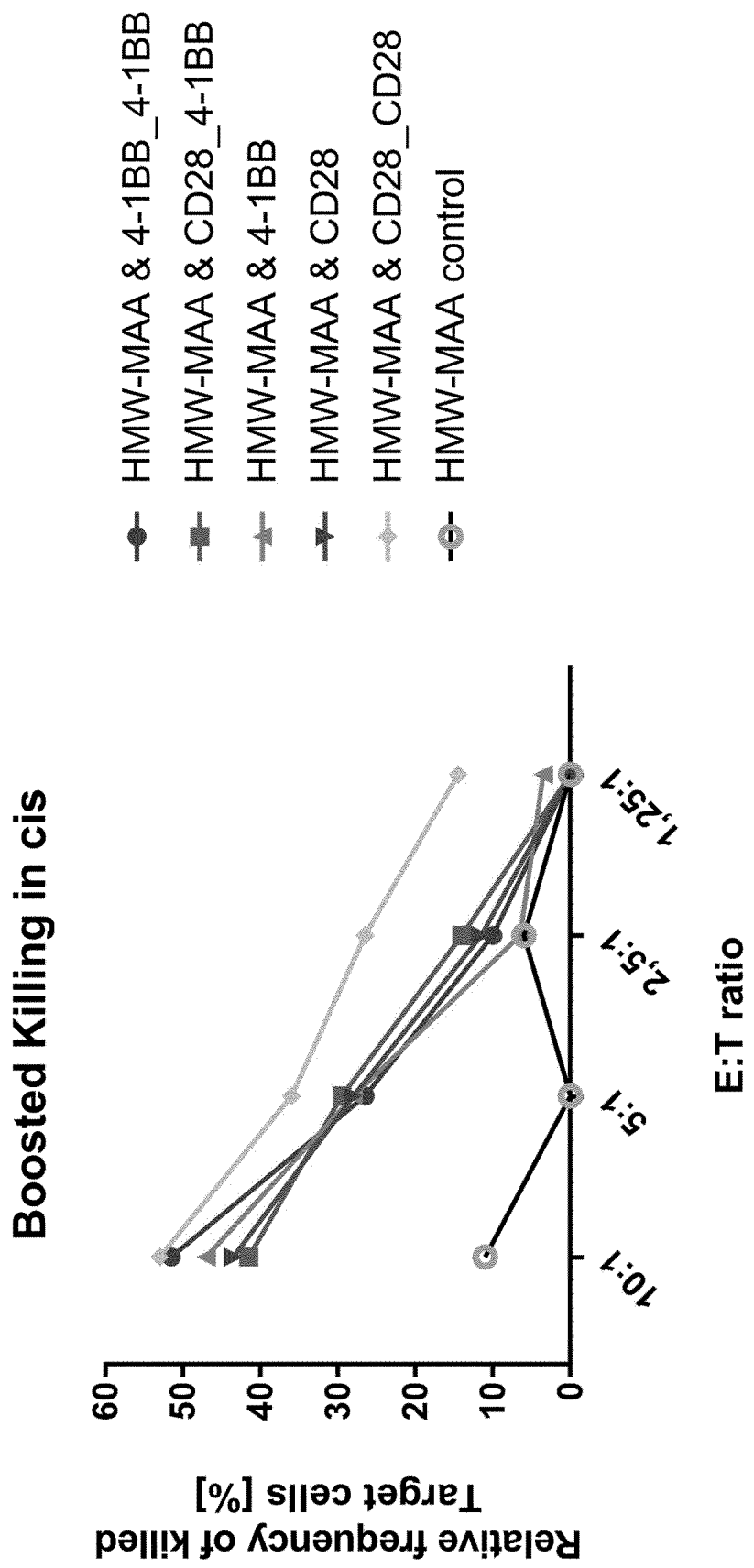
FIG. 8: Luminescence-based cytotoxicity assay. Anti-HMW-MAA CAR and anti-CD20 CCR (with either 4-1BB_4-1BB signaling, CD28_4-1BB signaling, 4-1BB signaling, CD28 signaling or CD28_CD28 signaling) co-expressing T cells and anti-HMW-MAA CAR T cells (HMW-MAA control) were co-cultured with transgenic Mel526 cells (HMW-MAA+ and CD20+) for 18 h. Subsequently, Luminescence was measured using a Luminescence plate reader.

3.3 Analyzing the Functionality in Cis or Trans Via a Luminescence-Based Killing Assay To determine the cytolytic activity of the generated CAR T cells, 2E4 Mel526$^{Luciferase\_eGFP}$ for the trans-approach or rather Mel526$^{Luciferase\_eGFP\_CD20}$ for the cis-approach were co-cultured with CAR/CCR T cells in different effector to target ratios (10:1; 5:1; 2,5:1; 1,25:1) in a total volume of 200 µl TexMACS Medium (Miltenyi Biotec) in 96-Blackwell plates (Miltenyi Biotec). For trans-testing, the same number of CD20-expressing cells (e.g. B cells, JeKo-1 or Raji) like T cells were added. After an incubation of 18 h, XenoLight D-Luciferin-K+ Salt Bioluminescent Substrate (PerkinElmer), diluted in TexMACS Medium (Miltenyi Biotec), was added to a final concentration of 300 µg/ml. Luminescence was measured using a Luminescence plate reader (PerkinElmer) (FIG. 8). Luminescence data correlates with viability and inversely correlates with target cell death as well-known in the art.

Example 4. Anti-LLE CAR Approaches 4.1 Generation of a Library of Lentiviral Transfer Vector Constructs Encoding Different Spacer Variants of the Anti-LLE CAR In order to generate anti-LLE CARs recognizing biotin, as well as parts of the linker moiety connecting biotin to antibody recognizing the target cell epitope, an scFv (single chain variable fragment) was designed based on the variable heavy (VH) and variable light (VL) chains of an anti-biotin antibody in VH-VL and VL-VH orientation (SEQ ID NO:17 and 18). Variable chains were connected by a flexible $(G_4S)_3$ linker and the human CD8 leader sequence (SEQ ID NO: 1) was placed N-terminally of the scFv and subcloned into transfer vector plasmids containing different spacer variants based on human IgG4 (HC) (SEQ ID NO: 5-7) and human CD8 stalk (SEQ ID NO: 8), a 2A element as well as an expression marker (ΔLNGFR) (SEQ ID NO: 12).

4.2 Generation of LV Particles, Transduction, Expansion, and Expression Analysis of Anti-LLE CAR T Cells LV particles were generated as already described under 1.2.

According to the protocol described under 1.3 T cells were prepared for the transduction with LV_anti-LLE CAR. On day 8 after activation, ΔLNGFR-expressing cells were separated by MACS using anti-ΔLNGFR microbeads on an LS column (Miltenyi Biotec) according to the manufacturer's instructions. Selected cells were reactivated using the T cell activation/expansion kit, human (Miltenyi Biotec) and seeded in a 24-well plate at a concentration of 1×10$^6$ cells/mL (2 mL per well). Cells were then continuously expanded and transduction efficiency was determined on day 14 after their first activation by flow analysis. For this an aliquot was removed and stained for ΔLNGFR expression using anti-ΔLNGFR APC (Miltenyi Biotec) according to the manufacturer's instructions.

4.3 Analyzing the Functionality of Anti-LLE CAR/CCR Modified T Cells

A xCELLigence kill assay, a luminescence-based killing assay as well as an intracellular Cytokine staining assay confirmed the cytolytic activity of the generated anti-LLE CAR T cells as previously documented in European patent application no. EP16196487.9, exemplified e.g. with the anti-LLE CAR comprising the SEQ ID NO: 22 or 23 that binds to 6-[6-(biotinamido)hexanamido] hexanoyl moiety (LLE) of the TCBM that binds an antigen on the surface of a target cell such as GD-2 or CD19.

The anti-LLE CAR/TCBM system is an example for the tag CAR system (universal CAR).

The cytolytic activity of this and other anti-LLE CAR expressing T cells can be enhanced and/or extended by activating a co-expressed chimeric costimulatory receptor, for instance the anti-CD20 CAR (described under 1.1) or the anti-dextran CAR to comparative levels as the CARs used under 1.1. In doing so, e.g. the anti-LLE CAR of SEQ ID NO: 22 can also be directed against above described TCBM that specifically binds to an antigen expressed on a cancer, e.g. a solid tumor, which is often surrounded by a hostile and immunosuppressive tumor microenvironment. Furthermore, the activation of the co-expressed chimeric costimulatory receptor can ensure the survival of the engineered T cell as soon as no TCBM is present, for example via the recognition of CD20 on omnipotent B cells by the anti-CD20 CAR.

The invention claimed is:

1. A T cell comprising:
   a) a chimeric antigen receptor (CAR) comprising a first antigen binding domain, a first transmembrane domain and a first cytoplasmic signaling domain comprising at least one CD3ζ cytoplasmic signaling domain and at least one 4-1BB co-stimulatory signaling domain, wherein said first antigen binding domain binds to a tag of a tagged polypeptide, and wherein the polypeptide of said tagged polypeptide binds to an antigen expressed on the surface of a target cell to be killed; and
   b) a chimeric costimulatory receptor (CCR) comprising a second antigen binding domain, a second transmembrane domain and a second cytoplasmic part comprising at least one CD28 co-stimulatory domain and/or at least one 4-1BB co-stimulatory domain or a combination thereof, wherein said CCR does not comprise CD3ζ, and wherein said second antigen binding domain binds to a further antigen, and wherein said further antigen is not expressed on the surface of said target cell.

2. The T cell according to claim 1, wherein said target cell is a cancer cell.

3. The T cell according to claim 1, wherein said second cytoplasmic part comprises two 4-1BB co-stimulatory domains or two CD28 co-stimulatory domains.

4. The T cell according to claim 1, wherein the polypeptide of said tagged polypeptide is an antibody or antigen binding fragment thereof, wherein said antibody or antigen binding fragment thereof binds to said antigen expressed on the surface of said target cell, and wherein the tag of said tagged polypeptide is a hapten.

5. The T cell according to claim 1, wherein the polypeptide of said tagged polypeptide is an antigen binding moiety (ABM), wherein the tag of said tagged polypeptide is a linker/label epitope (LLE) of a target cell binding molecule (TCBM), and wherein said CAR is an anti-linker/label epitope chimeric antigen receptor (anti-LLE CAR) comprising:
   I) an extracellular linker/label epitope (LLE) binding domain;
   II) a transmembrane domain; and
   III) a cytoplasmic signaling domain comprising at least one CD3ζ cytoplasmic signaling domain and at least one 4-1BB co-stimulatory signaling domain,
   wherein said extracellular LLE binding domain binds a target cell binding molecule (TCBM) comprising:
   i) an antigen binding moiety (ABM), wherein said ABM binds specifically to said antigen expressed on the surface of said target cell;
   ii) a label moiety (LaM), wherein said LaM is a naturally occurring molecule in a subject or a derivative thereof; and
   iii) a linker moiety (LiM) conjugating said ABM and said LaM, thereby forming a linker/label epitope (LLE),
   wherein said extracellular LLE binding domain binds said LLE with a higher preference than said naturally occurring molecule.

6. The T cell according to claim 1, wherein said further antigen is expressed on the surface of another cell that is not in a disease state.

7. The T cell according to claim 6, wherein said further antigen is CD20 and the other cell is a B cell.

8. The T cell according to claim 1, wherein said further antigen is not expressed on a surface of a cell.

9. The T cell according to claim 8, wherein said further antigen is dextran.

10. The T cell according to claim 9, wherein said second antigen binding domain comprises the amino acid sequence of SEQ ID NO: 19, and wherein said second cytoplasmic part comprises the amino acid sequence of SEQ ID NO: 21.

* * * * *

SEQUENCE LISTING

```
<160> NUMBER OF SEQ ID NOS: 23

<210> SEQ ID NO 1
<211> LENGTH: 22
<212> TYPE: PRT
<213> ORGANISM: Artificial sequence
<220> FEATURE:
<223> OTHER INFORMATION: human CD8 leader sequence

<400> SEQUENCE: 1

Met Asp Phe Gln Val Gln Ile Phe Ser Phe Leu Leu Ile Ser Ala Ser
1               5                   10                  15

Val Ile Met Ser Arg Gly
            20

<210> SEQ ID NO 2
<211> LENGTH: 21
<212> TYPE: PRT
<213> ORGANISM: Artificial sequence
<220> FEATURE:
<223> OTHER INFORMATION: murine lkappa leader protein
```

-continued

```
<400> SEQUENCE: 2

Met Asp Phe Gln Val Gln Ile Phe Ser Phe Leu Leu Ile Ser Ala Ser
1               5                   10                  15

Val Ile Met Ser Arg
            20

<210> SEQ ID NO 3
<211> LENGTH: 252
<212> TYPE: PRT
<213> ORGANISM: Artificial sequence
<220> FEATURE:
<223> OTHER INFORMATION: 225.28s scFv VL_(G4S)3_VH

<400> SEQUENCE: 3

Asp Ile Glu Leu Thr Gln Ser Pro Lys Phe Met Ser Thr Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Glu Pro Leu Leu
        35                  40                  45

Phe Ser Ala Ser Tyr Arg Tyr Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Gly Gly Thr Lys Leu Glu Ile Lys Arg Ala Ala Ala Glu
            100                 105                 110

Gly Gly Gly Gly Ser Gly Gly Gly Ser Gly Gly Gly Gly Ser Ala
        115                 120                 125

Met Ala Gln Val Lys Leu Gln Gln Ser Gly Gly Gly Leu Val Gln Pro
    130                 135                 140

Gly Gly Ser Met Lys Leu Ser Cys Val Val Ser Gly Phe Thr Phe Ser
145                 150                 155                 160

Asn Tyr Trp Met Asn Trp Val Arg Gln Ser Pro Glu Lys Gly Leu Glu
                165                 170                 175

Trp Ile Ala Glu Ile Arg Leu Lys Ser Asn Asn Phe Gly Arg Tyr Tyr
            180                 185                 190

Ala Glu Ser Val Lys Gly Arg Phe Thr Ile Ser Arg Asp Asp Ser Lys
        195                 200                 205

Ser Ser Ala Tyr Leu Gln Met Ile Asn Leu Arg Ala Glu Asp Thr Gly
    210                 215                 220

Ile Tyr Tyr Cys Thr Ser Tyr Gly Asn Tyr Val Gly His Tyr Phe Asp
225                 230                 235                 240

His Trp Gly Gln Gly Thr Thr Val Thr Val Ser Ser
                245                 250

<210> SEQ ID NO 4
<211> LENGTH: 259
<212> TYPE: PRT
<213> ORGANISM: Artificial sequence
<220> FEATURE:
<223> OTHER INFORMATION: 763.74 scFv VH_(G4S)3_VL
```

-continued

```
<400> SEQUENCE: 4

Met Glu Phe Gly Leu Ser Trp Leu Phe Leu Val Ala Ile Leu Lys Gly
1               5                   10                  15

Val Gln Cys Ser Arg Met Ala Gln Val Lys Leu Lys Glu Ser Gly Pro
            20                  25                  30

Glu Leu Lys Lys Pro Gly Glu Thr Val Lys Ile Ser Cys Lys Ala Ser
        35                  40                  45

Gly Tyr Thr Phe Thr Asp Tyr Ser Met His Trp Val Lys Lys Thr Pro
50                  55                  60

Gly Lys Gly Leu Lys Trp Leu Gly Trp Ile Asn Thr Ala Thr Gly Glu
65                  70                  75                  80

Pro Thr Tyr Ala Asp Asp Phe Lys Gly Arg Phe Ala Ile Ser Leu Glu
                85                  90                  95

Thr Ser Ala Arg Thr Val Tyr Leu Gln Ile Asn Asn Leu Arg Asn Glu
            100                 105                 110

Asp Thr Ala Thr Tyr Phe Cys Phe Ser Tyr Tyr Asp Tyr Trp Gly Gln
        115                 120                 125

Gly Thr Thr Val Thr Val Ser Ser Gly Gly Gly Gly Ser Gly Gly Gly
130                 135                 140

Gly Ser Gly Gly Gly Gly Leu Asp Ile Lys Leu Thr Gln Ser Pro Ser
145                 150                 155                 160

Ile Leu Ser Val Thr Pro Gly Glu Thr Val Ser Leu Ser Cys Arg Ala
                165                 170                 175

Ser Gln Thr Ile Tyr Lys Asn Leu His Trp Tyr Gln Gln Lys Ser His
            180                 185                 190

Arg Ser Pro Arg Leu Leu Tyr Lys Tyr Gly Ser Asp Ser Ile Ser Gly
        195                 200                 205

Ile Pro Ser Arg Phe Thr Gly Ser Gly Ser Gly Thr Asp Tyr Thr Leu
210                 215                 220

Asn Ile Asn Ser Val Lys Pro Glu Asp Glu Gly Ile Tyr Tyr Cys Leu
225                 230                 235                 240

Gln Gly Tyr Ser Thr Pro Trp Thr Phe Gly Gly Gly Thr Lys Leu Glu
                245                 250                 255

Ile Lys Arg

<210> SEQ ID NO 5
<211> LENGTH: 228
<212> TYPE: PRT
<213> ORGANISM: Artificial sequence
<220> FEATURE:
<223> OTHER INFORMATION: human Spacer IgG4 Hinge_CH2_CH3

<400> SEQUENCE: 5

Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Gln Ser Thr
65                  70                  75                  80

Tyr Arg Val Val Ser Val Leu Thr Val Leu His Gln Asp Trp Leu Asn
                85                  90                  95
```

```
Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys
225

<210> SEQ ID NO 6
<211> LENGTH: 119
<212> TYPE: PRT
<213> ORGANISM: Artificial sequence
<220> FEATURE:
<223> OTHER INFORMATION: human Spacer IgG4 Hinge_ CH3

<400> SEQUENCE: 6

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115

<210> SEQ ID NO 7
<211> LENGTH: 12
<212> TYPE: PRT
<213> ORGANISM: Artificial sequence
<220> FEATURE:
<223> OTHER INFORMATION: human Spacer IgG4 Hinge

<400> SEQUENCE: 7

Glu Ser Lys Tyr Gly Pro Pro Cys Pro Pro Cys Pro
1               5                   10

<210> SEQ ID NO 8
<211> LENGTH: 45
<212> TYPE: PRT
<213> ORGANISM: Artificial sequence
```

<220> FEATURE:
<223> OTHER INFORMATION: human CD8 stalk

<400> SEQUENCE: 8

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 9
<211> LENGTH: 24
<212> TYPE: PRT
<213> ORGANISM: Artificial sequence
<220> FEATURE:
<223> OTHER INFORMATION: human CD8 transmembrane domain

<400> SEQUENCE: 9

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 10
<211> LENGTH: 42
<212> TYPE: PRT
<213> ORGANISM: Artificial sequence
<220> FEATURE:
<223> OTHER INFORMATION: human 4-1BB intracellular domain

<400> SEQUENCE: 10

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 11
<211> LENGTH: 112
<212> TYPE: PRT
<213> ORGANISM: Artificial sequence
<220> FEATURE:
<223> OTHER INFORMATION: human CD3 signaling domain

<400> SEQUENCE: 11

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 12
<211> LENGTH: 302
<212> TYPE: PRT
<213> ORGANISM: Artificial sequence
<220> FEATURE:
<223> OTHER INFORMATION: 2A-element linked LNGFR

<400> SEQUENCE: 12

Arg Ala Lys Arg Ser Ala Gly Ser Gly Ala Thr Asn Phe Ser Leu Leu
1               5                   10                  15

Lys Gln Ala Gly Asp Val Glu Glu Asn Pro Gly Pro Met Gly Ala Gly
            20                  25                  30

Ala Thr Gly Arg Ala Met Asp Gly Pro Arg Leu Leu Leu Leu Leu Leu
        35                  40                  45

Leu Gly Val Ser Leu Gly Gly Ala Lys Glu Ala Cys Pro Thr Gly Leu
    50                  55                  60

Tyr Thr His Ser Gly Glu Cys Cys Lys Ala Cys Asn Leu Gly Glu Gly
65                  70                  75                  80

Val Ala Gln Pro Cys Gly Ala Asn Gln Thr Val Cys Glu Pro Cys Leu
                85                  90                  95

Asp Ser Val Thr Phe Ser Asp Val Val Ser Ala Thr Glu Pro Cys Lys
            100                 105                 110

Pro Cys Thr Glu Cys Val Gly Leu Gln Ser Met Ser Ala Pro Cys Val
        115                 120                 125

Glu Ala Asp Asp Ala Val Cys Arg Cys Ala Tyr Gly Tyr Tyr Gln Asp
    130                 135                 140

Glu Thr Thr Gly Arg Cys Glu Ala Cys Arg Val Cys Glu Ala Gly Ser
145                 150                 155                 160

Gly Leu Val Phe Ser Cys Gln Asp Lys Gln Asn Thr Val Cys Glu Glu
                165                 170                 175

Cys Pro Asp Gly Thr Tyr Ser Asp Glu Ala Asn His Val Asp Pro Cys
            180                 185                 190

Leu Pro Cys Thr Val Cys Glu Asp Thr Glu Arg Gln Leu Arg Glu Cys
        195                 200                 205

Thr Arg Trp Ala Asp Ala Glu Cys Glu Glu Ile Pro Gly Arg Trp Ile
    210                 215                 220

Thr Arg Ser Thr Pro Pro Glu Gly Ser Asp Ser Thr Ala Pro Ser Thr
225                 230                 235                 240

Gln Glu Pro Glu Ala Pro Pro Glu Gln Asp Leu Ile Ala Ser Thr Val
                245                 250                 255

Ala Gly Val Val Thr Thr Val Met Gly Ser Ser Gln Pro Val Val Thr
            260                 265                 270

Arg Gly Thr Thr Asp Asn Leu Ile Pro Val Tyr Cys Ser Ile Leu Ala
        275                 280                 285

Ala Val Val Val Gly Leu Val Ala Tyr Ile Ala Phe Lys Arg
    290                 295                 300

<210> SEQ ID NO 13
<211> LENGTH: 243
<212> TYPE: PRT
<213> ORGANISM: Artificial sequence
<220> FEATURE:
<223> OTHER INFORMATION: anti CD20 scFv VL_(G4S)3_VH

<400> SEQUENCE: 13

```
Asp Ile Val Leu Thr Gln Ser Pro Ala Ile Leu Ser Ala Ser Pro Gly
1               5                   10                  15
Glu Lys Val Thr Met Thr Cys Arg Ala Ser Ser Ser Val Asn Tyr Met
            20                  25                  30
Asp Trp Tyr Gln Lys Pro Gly Ser Ser Pro Lys Pro Trp Ile Tyr
        35                  40                  45
Ala Thr Ser Asn Leu Ala Ser Gly Val Pro Ala Arg Phe Ser Gly Ser
    50                  55                  60
Gly Ser Gly Thr Ser Tyr Ser Leu Thr Ile Ser Arg Val Glu Ala Glu
65                  70                  75                  80
Asp Ala Ala Thr Tyr Tyr Cys Gln Gln Trp Ser Phe Asn Pro Pro Thr
                85                  90                  95
Phe Gly Gly Gly Thr Lys Leu Glu Ile Lys Gly Gly Gly Gly Ser Gly
            100                 105                 110
Gly Gly Gly Ser Gly Gly Gly Ser Glu Val Gln Leu Gln Gln Ser
        115                 120                 125
Gly Ala Glu Leu Val Lys Pro Gly Ala Ser Val Lys Met Ser Cys Lys
    130                 135                 140
Ala Ser Gly Tyr Thr Phe Thr Ser Tyr Asn Met His Trp Val Lys Gln
145                 150                 155                 160
Thr Pro Gly Gln Gly Leu Glu Trp Ile Gly Ala Ile Tyr Pro Gly Asn
                165                 170                 175
Gly Asp Thr Ser Tyr Asn Gln Lys Phe Lys Gly Lys Ala Thr Leu Thr
            180                 185                 190
Ala Asp Lys Ser Ser Ser Thr Ala Tyr Met Gln Leu Ser Ser Leu Thr
        195                 200                 205
Ser Glu Asp Ser Ala Asp Tyr Tyr Cys Ala Arg Ser Asn Tyr Tyr Gly
    210                 215                 220
Ser Ser Tyr Trp Phe Phe Asp Val Trp Gly Ala Gly Thr Thr Val Thr
225                 230                 235                 240
Val Ser Ser
```

<210> SEQ ID NO 14
<211> LENGTH: 231
<212> TYPE: PRT
<213> ORGANISM: Artificial sequence
<220> FEATURE:
<223> OTHER INFORMATION: human Spacer IgG1 Hinge_CH2_CH3

<400> SEQUENCE: 14

```
Glu Pro Lys Ser Ser Asp Lys Thr His Thr Cys Pro Pro Cys Pro Ala
1               5                   10                  15
Pro Pro Val Ala Gly Pro Ser Val Phe Leu Phe Pro Pro Lys Pro Lys
            20                  25                  30
Asp Thr Leu Met Ile Ala Arg Thr Pro Glu Val Thr Cys Val Val Val
        35                  40                  45
Asp Val Ser His Glu Asp Pro Glu Val Lys Phe Asn Trp Tyr Val Asp
    50                  55                  60
Gly Val Glu Val His Asn Ala Lys Thr Lys Pro Arg Glu Glu Gln Tyr
65                  70                  75                  80
Asn Ser Thr Tyr Arg Val Val Ser Val Leu Thr Val Leu His Gln Asp
                85                  90                  95
Trp Leu Asn Gly Lys Glu Tyr Lys Cys Lys Val Ser Asn Lys Ala Leu
            100                 105                 110
```

```
Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Asp Glu Leu Thr Lys
        130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
210                 215                 220

Leu Ser Leu Ser Pro Gly Lys
225                 230

<210> SEQ ID NO 15
<211> LENGTH: 698
<212> TYPE: PRT
<213> ORGANISM: Artificial sequence
<220> FEATURE:
<223> OTHER INFORMATION: 2A-element linked  EGFR

<400> SEQUENCE: 15

Arg Ala Lys Arg Ser Ala Gly Ser Gly Ala Thr Asn Phe Ser Leu Leu
1               5                   10                  15

Lys Gln Ala Gly Asp Val Glu Glu Asn Pro Gly Pro Ala Ser Met Arg
            20                  25                  30

Pro Ser Gly Thr Ala Gly Ala Ala Leu Leu Ala Leu Leu Ala Ala Leu
        35                  40                  45

Cys Pro Ala Ser Arg Ala Leu Glu Glu Lys Lys Val Cys Gln Gly Thr
    50                  55                  60

Ser Asn Lys Leu Thr Gln Leu Gly Thr Phe Glu Asp His Phe Leu Ser
65                  70                  75                  80

Leu Gln Arg Met Phe Asn Asn Cys Glu Val Val Leu Gly Asn Leu Glu
                85                  90                  95

Ile Thr Tyr Val Gln Arg Asn Tyr Asp Leu Ser Phe Leu Lys Thr Ile
            100                 105                 110

Gln Glu Val Ala Gly Tyr Val Leu Ile Ala Leu Asn Thr Val Glu Arg
        115                 120                 125

Ile Pro Leu Glu Asn Leu Gln Ile Ile Arg Gly Asn Met Tyr Tyr Glu
    130                 135                 140

Asn Ser Tyr Ala Leu Ala Val Leu Ser Asn Tyr Asp Ala Asn Lys Thr
145                 150                 155                 160

Gly Leu Lys Glu Leu Pro Met Arg Asn Leu Gln Glu Ile Leu His Gly
                165                 170                 175

Ala Val Arg Phe Ser Asn Asn Pro Ala Leu Cys Asn Val Glu Ser Ile
            180                 185                 190

Gln Trp Arg Asp Ile Val Ser Ser Asp Phe Leu Ser Asn Met Ser Met
        195                 200                 205

Asp Phe Gln Asn His Leu Gly Ser Cys Gln Lys Cys Asp Pro Ser Cys
    210                 215                 220

Pro Asn Gly Ser Cys Trp Gly Ala Gly Glu Glu Asn Cys Gln Lys Leu
225                 230                 235                 240
```

```
-continued

Thr Lys Ile Ile Cys Ala Gln Gln Cys Ser Gly Arg Cys Arg Gly Lys
                245                 250                 255

Ser Pro Ser Asp Cys Cys His Asn Gln Cys Ala Ala Gly Cys Thr Gly
            260                 265                 270

Pro Arg Glu Ser Asp Cys Leu Val Cys Arg Lys Phe Arg Asp Glu Ala
        275                 280                 285

Thr Cys Lys Asp Thr Cys Pro Pro Leu Met Leu Tyr Asn Pro Thr Thr
    290                 295                 300

Tyr Gln Met Asp Val Asn Pro Glu Gly Lys Tyr Ser Phe Gly Ala Thr
305                 310                 315                 320

Cys Val Lys Lys Cys Pro Arg Asn Tyr Val Val Thr Asp His Gly Ser
                325                 330                 335

Cys Val Arg Ala Cys Gly Ala Asp Ser Tyr Glu Met Glu Glu Asp Gly
            340                 345                 350

Val Arg Lys Cys Lys Lys Cys Glu Gly Pro Cys Arg Lys Val Cys Asn
        355                 360                 365

Gly Ile Gly Ile Gly Glu Phe Lys Asp Ser Leu Ser Ile Asn Ala Thr
    370                 375                 380

Asn Ile Lys His Phe Lys Asn Cys Thr Ser Ile Ser Gly Asp Leu His
385                 390                 395                 400

Ile Leu Pro Val Ala Phe Arg Gly Asp Ser Phe Thr His Thr Pro Pro
                405                 410                 415

Leu Asp Pro Gln Glu Leu Asp Ile Leu Lys Thr Val Lys Glu Ile Thr
            420                 425                 430

Gly Phe Leu Leu Ile Gln Ala Trp Pro Glu Asn Arg Thr Asp Leu His
        435                 440                 445

Ala Phe Glu Asn Leu Glu Ile Ile Arg Gly Arg Thr Lys Gln His Gly
    450                 455                 460

Gln Phe Ser Leu Ala Val Val Ser Leu Asn Ile Thr Ser Leu Gly Leu
465                 470                 475                 480

Arg Ser Leu Lys Glu Ile Ser Asp Gly Asp Val Ile Ile Ser Gly Asn
                485                 490                 495

Lys Asn Leu Cys Tyr Ala Asn Thr Ile Asn Trp Lys Lys Leu Phe Gly
            500                 505                 510

Thr Ser Gly Gln Lys Thr Lys Ile Ile Ser Asn Arg Gly Glu Asn Ser
        515                 520                 525

Cys Lys Ala Thr Gly Gln Val Cys His Ala Leu Cys Ser Pro Glu Gly
    530                 535                 540

Cys Trp Gly Pro Glu Pro Arg Asp Cys Val Ser Cys Arg Asn Val Ser
545                 550                 555                 560

Arg Gly Arg Glu Cys Val Asp Lys Cys Asn Leu Leu Glu Gly Glu Pro
                565                 570                 575

Arg Glu Phe Val Glu Asn Ser Glu Cys Ile Gln Cys His Pro Glu Cys
            580                 585                 590

Leu Pro Gln Ala Met Asn Ile Thr Cys Thr Gly Arg Gly Pro Asp Asn
        595                 600                 605

Cys Ile Gln Cys Ala His Tyr Ile Asp Gly Pro His Cys Val Lys Thr
    610                 615                 620

Cys Pro Ala Gly Val Met Gly Glu Asn Asn Thr Leu Val Trp Lys Tyr
625                 630                 635                 640

Ala Asp Ala Gly His Val Cys His Leu Cys His Pro Asn Cys Thr Tyr
                645                 650                 655
```

```
Gly Cys Thr Gly Pro Gly Leu Glu Gly Cys Pro Thr Asn Gly Pro Lys
            660                 665                 670

Ile Pro Ser Ile Ala Thr Gly Met Val Gly Ala Leu Leu Leu Leu Leu
        675                 680                 685

Val Val Ala Leu Gly Ile Gly Leu Phe Met
    690                 695

<210> SEQ ID NO 16
<211> LENGTH: 41
<212> TYPE: PRT
<213> ORGANISM: Artificial sequence
<220> FEATURE:
<223> OTHER INFORMATION: CD28 intracellular domain

<400> SEQUENCE: 16

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 17
<211> LENGTH: 249
<212> TYPE: PRT
<213> ORGANISM: Artificial sequence
<220> FEATURE:
<223> OTHER INFORMATION: Anti-Biotin antibody VH_(G4S)3_VL

<400> SEQUENCE: 17

Glu Val Gln Leu Val Glu Ser Gly Gly Gly Leu Val Lys Pro Gly Gly
1               5                   10                  15

Ser Leu Lys Leu Ser Cys Ala Val Ser Gly Phe Thr Phe Ser Asn Tyr
            20                  25                  30

Ala Met Ser Trp Val Arg Gln Thr Pro Glu Thr Arg Leu Asn Trp Val
        35                  40                  45

Ala Thr Ile Thr Gly Gly Gly Ser Tyr Thr Tyr Tyr Pro Asp Ser Val
    50                  55                  60

Lys Gly Arg Phe Thr Ile Ser Arg Asp Asn Ala Lys Asp Thr Leu Tyr
65                  70                  75                  80

Leu Gln Met Ser Ser Leu Arg Ser Glu Asp Thr Ala Met Tyr Tyr Cys
                85                  90                  95

Val Arg Gln Arg Val Gly Asp Tyr Val Ser Ser Leu Leu Gly Tyr Trp
            100                 105                 110

Gly Gln Gly Thr Leu Val Thr Val Ser Ala Gly Gly Gly Gly Ser Gly
        115                 120                 125

Gly Gly Gly Ser Gly Gly Gly Gly Ser Asp Val Val Met Thr Gln Thr
    130                 135                 140

Pro Leu Ser Leu Pro Val Ser Leu Gly Asp Gln Ala Ser Ile Ser Cys
145                 150                 155                 160

Arg Ser Ser Gln Ser Leu Val His Ser Asn Gly Asn Thr Tyr Leu His
                165                 170                 175

Trp Phe Leu Gln Lys Pro Gly Ser Pro Asn Leu Leu Ile Tyr Lys
            180                 185                 190

Val Ser Asn Arg Phe Ser Gly Val Pro Asp Arg Phe Ser Gly Ser Gly
        195                 200                 205

Ser Gly Thr Asp Phe Thr Leu Lys Ile Ser Arg Val Glu Ala Glu Asp
    210                 215                 220
```

```
Leu Gly Val Tyr Phe Cys Ser Gln Ser Thr His Val Pro Tyr Thr Phe
225                 230                 235                 240

Gly Gly Gly Thr Lys Leu Glu Ile Lys
            245

<210> SEQ ID NO 18
<211> LENGTH: 249
<212> TYPE: PRT
<213> ORGANISM: Artificial sequence
<220> FEATURE:
<223> OTHER INFORMATION: Anti-Biotin scFv VL_(G4S)3_VH

<400> SEQUENCE: 18

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Phe Leu Gln Lys Pro Gly Gln Ser
        35                  40                  45

Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

Gly Gly Gly Gly Ser Gly Gly Gly Gly Ser Gly Gly Gly Gly Ser Glu
        115                 120                 125

Val Gln Leu Val Glu Ser Gly Gly Gly Leu Val Lys Pro Gly Gly Ser
    130                 135                 140

Leu Lys Leu Ser Cys Ala Val Ser Gly Phe Thr Phe Ser Asn Tyr Ala
145                 150                 155                 160

Met Ser Trp Val Arg Gln Thr Pro Glu Thr Arg Leu Asn Trp Val Ala
                165                 170                 175

Thr Ile Thr Gly Gly Gly Ser Tyr Thr Tyr Tyr Pro Asp Ser Val Lys
            180                 185                 190

Gly Arg Phe Thr Ile Ser Arg Asp Asn Ala Lys Asp Thr Leu Tyr Leu
        195                 200                 205

Gln Met Ser Ser Leu Arg Ser Glu Asp Thr Ala Met Tyr Tyr Cys Val
    210                 215                 220

Arg Gln Arg Val Gly Asp Tyr Val Ser Ser Leu Leu Gly Tyr Trp Gly
225                 230                 235                 240

Gln Gly Thr Leu Val Thr Val Ser Ala
            245

<210> SEQ ID NO 19
<211> LENGTH: 238
<212> TYPE: PRT
<213> ORGANISM: Artificial sequence
<220> FEATURE:
<223> OTHER INFORMATION: Anti-Dextran scFv VH_(G4S)3_VL

<400> SEQUENCE: 19

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30
```

```
Tyr Met Asn Trp Val Lys Gln Ser His Gly Lys Ser Leu Glu Trp Ile
             35                  40                  45

Gly Asp Ile Asn Pro Asn Asn Gly Gly Thr Ser Tyr Asn Gln Lys Phe
 50                  55                  60

Lys Gly Lys Ala Thr Leu Thr Val Asp Lys Ser Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Pro Tyr Tyr Tyr Thr Ser Ser Leu Val Trp Gly Thr Gly Thr Thr
            100                 105                 110

Val Thr Val Ser Ala Gly Gly Gly Ser Gly Gly Gly Ser Gly
            115                 120                 125

Gly Gly Gly Ser Gln Ile Val Leu Thr Gln Ser Pro Ala Ile Met Ser
130                 135                 140

Ala Ser Pro Gly Glu Lys Val Thr Met Thr Cys Ser Ala Ser Ser Ser
145                 150                 155                 160

Val Ser Tyr Met His Trp Tyr Gln Gln Lys Ser Gly Thr Ser Pro Lys
            165                 170                 175

Arg Trp Ile Tyr Asp Thr Ser Lys Leu Ala Ser Gly Val Pro Ala Arg
            180                 185                 190

Phe Ser Gly Ser Gly Ser Gly Thr Ser Tyr Ser Leu Thr Ile Ser Ser
            195                 200                 205

Met Glu Ala Glu Asp Ala Ala Thr Tyr Tyr Cys Gln Gln Trp Ser Ser
            210                 215                 220

Asn Pro Leu Thr Phe Gly Ala Gly Thr Lys Leu Glu Leu Lys
225                 230                 235

<210> SEQ ID NO 20
<211> LENGTH: 1307
<212> TYPE: PRT
<213> ORGANISM: Artificial sequence
<220> FEATURE:
<223> OTHER INFORMATION: Anti-CD20 CCR (CD8Leader-anti-CD20VL/VH-
      Spacer5-CD8TM-41BB-4-1BB)

<400> SEQUENCE: 20

Met Ala Leu Pro Val Thr Ala Leu Leu Leu Pro Leu Ala Leu Leu Leu
 1               5                  10                  15

His Ala Ala Arg Pro Asp Ile Val Leu Thr Gln Ser Pro Ala Ile Leu
                 20                  25                  30

Ser Ala Ser Pro Gly Glu Lys Val Thr Met Thr Cys Arg Ala Ser Ser
             35                  40                  45

Ser Val Asn Tyr Met Asp Trp Tyr Gln Lys Lys Pro Gly Ser Ser Pro
 50                  55                  60

Lys Pro Trp Ile Tyr Ala Thr Ser Asn Leu Ala Ser Gly Val Pro Ala
 65                  70                  75                  80

Arg Phe Ser Gly Ser Gly Ser Gly Thr Ser Tyr Ser Leu Thr Ile Ser
                 85                  90                  95

Arg Val Glu Ala Glu Asp Ala Ala Thr Tyr Tyr Cys Gln Gln Trp Ser
            100                 105                 110

Phe Asn Pro Pro Thr Phe Gly Gly Gly Thr Lys Leu Glu Ile Lys Gly
            115                 120                 125

Gly Gly Ser Gly Gly Gly Gly Ser Gly Gly Gly Ser Glu Val
130                 135                 140

Gln Leu Gln Gln Ser Gly Ala Glu Leu Val Lys Pro Gly Ala Ser Val
145                 150                 155                 160
```

-continued

Lys Met Ser Cys Lys Ala Ser Gly Tyr Thr Phe Thr Ser Tyr Asn Met
                165                 170                 175
His Trp Val Lys Gln Thr Pro Gly Gln Gly Leu Glu Trp Ile Gly Ala
            180                 185                 190
Ile Tyr Pro Gly Asn Gly Asp Thr Ser Tyr Asn Gln Lys Phe Lys Gly
        195                 200                 205
Lys Ala Thr Leu Thr Ala Asp Lys Ser Ser Thr Ala Tyr Met Gln
210                 215                 220
Leu Ser Ser Leu Thr Ser Glu Asp Ser Ala Asp Tyr Tyr Cys Ala Arg
225                 230                 235                 240
Ser Asn Tyr Tyr Gly Ser Ser Tyr Trp Phe Phe Asp Val Trp Gly Ala
                245                 250                 255
Gly Thr Thr Val Thr Val Ser Ser Glu Pro Lys Ser Ser Asp Lys Thr
            260                 265                 270
His Thr Cys Pro Pro Cys Pro Ala Pro Pro Val Ala Gly Pro Ser Val
        275                 280                 285
Phe Leu Phe Pro Pro Lys Pro Lys Asp Thr Leu Met Ile Ala Arg Thr
290                 295                 300
Pro Glu Val Thr Cys Val Val Val Asp Val Ser His Glu Asp Pro Glu
305                 310                 315                 320
Val Lys Phe Asn Trp Tyr Val Asp Gly Val Glu Val His Asn Ala Lys
                325                 330                 335
Thr Lys Pro Arg Glu Glu Gln Tyr Asn Ser Thr Tyr Arg Val Val Ser
            340                 345                 350
Val Leu Thr Val Leu His Gln Asp Trp Leu Asn Gly Lys Glu Tyr Lys
        355                 360                 365
Cys Lys Val Ser Asn Lys Ala Leu Pro Ala Pro Ile Glu Lys Thr Ile
370                 375                 380
Ser Lys Ala Lys Gly Gln Pro Arg Glu Pro Gln Val Tyr Thr Leu Pro
385                 390                 395                 400
Pro Ser Arg Asp Glu Leu Thr Lys Asn Gln Val Ser Leu Thr Cys Leu
                405                 410                 415
Val Lys Gly Phe Tyr Pro Ser Asp Ile Ala Val Glu Trp Glu Ser Asn
            420                 425                 430
Gly Gln Pro Glu Asn Asn Tyr Lys Thr Thr Pro Pro Val Leu Asp Ser
        435                 440                 445
Asp Gly Ser Phe Phe Leu Tyr Ser Lys Leu Thr Val Asp Lys Ser Arg
450                 455                 460
Trp Gln Gln Gly Asn Val Phe Ser Cys Ser Val Met His Glu Ala Leu
465                 470                 475                 480
His Asn His Tyr Thr Gln Lys Ser Leu Ser Leu Ser Pro Gly Lys Ile
                485                 490                 495
Tyr Ile Trp Ala Pro Leu Ala Gly Thr Cys Gly Val Leu Leu Leu Ser
            500                 505                 510
Leu Val Ile Thr Leu Tyr Cys Leu Gln Lys Arg Gly Arg Lys Lys Leu
        515                 520                 525
Leu Tyr Ile Phe Lys Gln Pro Phe Met Arg Pro Val Gln Thr Thr Gln
530                 535                 540
Glu Glu Asp Gly Cys Ser Cys Arg Phe Pro Glu Glu Glu Glu Gly Gly
545                 550                 555                 560
Cys Glu Leu Ser Thr Lys Arg Gly Arg Lys Lys Leu Leu Tyr Ile Phe
                565                 570                 575

```
Lys Gln Pro Phe Met Arg Pro Val Gln Thr Thr Gln Glu Glu Asp Gly
            580                 585                 590

Cys Ser Cys Arg Phe Pro Glu Glu Glu Gly Gly Cys Glu Leu His
            595                 600                 605

Val Arg Ala Lys Arg Ser Ala Gly Ser Gly Ala Thr Asn Phe Ser Leu
            610                 615                 620

Leu Lys Gln Ala Gly Asp Val Glu Glu Asn Pro Gly Pro Ala Ser Met
625                 630                 635                 640

Arg Pro Ser Gly Thr Ala Gly Ala Ala Leu Leu Ala Leu Leu Ala Ala
                    645                 650                 655

Leu Cys Pro Ala Ser Arg Ala Leu Glu Glu Lys Lys Val Cys Gln Gly
            660                 665                 670

Thr Ser Asn Lys Leu Thr Gln Leu Gly Thr Phe Glu Asp His Phe Leu
            675                 680                 685

Ser Leu Gln Arg Met Phe Asn Asn Cys Glu Val Val Leu Gly Asn Leu
            690                 695                 700

Glu Ile Thr Tyr Val Gln Arg Asn Tyr Asp Leu Ser Phe Leu Lys Thr
705                 710                 715                 720

Ile Gln Glu Val Ala Gly Tyr Val Leu Ile Ala Leu Asn Thr Val Glu
                    725                 730                 735

Arg Ile Pro Leu Glu Asn Leu Gln Ile Ile Arg Gly Asn Met Tyr Tyr
            740                 745                 750

Glu Asn Ser Tyr Ala Leu Ala Val Leu Ser Asn Tyr Asp Ala Asn Lys
            755                 760                 765

Thr Gly Leu Lys Glu Leu Pro Met Arg Asn Leu Gln Glu Ile Leu His
770                 775                 780

Gly Ala Val Arg Phe Ser Asn Asn Pro Ala Leu Cys Asn Val Glu Ser
785                 790                 795                 800

Ile Gln Trp Arg Asp Ile Val Ser Ser Asp Phe Leu Ser Asn Met Ser
            805                 810                 815

Met Asp Phe Gln Asn His Leu Gly Ser Cys Gln Lys Cys Asp Pro Ser
            820                 825                 830

Cys Pro Asn Gly Ser Cys Trp Gly Ala Gly Glu Glu Asn Cys Gln Lys
            835                 840                 845

Leu Thr Lys Ile Ile Cys Ala Gln Gln Cys Ser Gly Arg Cys Arg Gly
850                 855                 860

Lys Ser Pro Ser Asp Cys Cys His Asn Gln Cys Ala Ala Gly Cys Thr
865                 870                 875                 880

Gly Pro Arg Glu Ser Asp Cys Leu Val Cys Arg Lys Phe Arg Asp Glu
            885                 890                 895

Ala Thr Cys Lys Asp Thr Cys Pro Pro Leu Met Leu Tyr Asn Pro Thr
            900                 905                 910

Thr Tyr Gln Met Asp Val Asn Pro Glu Gly Lys Tyr Ser Phe Gly Ala
            915                 920                 925

Thr Cys Val Lys Lys Cys Pro Arg Asn Tyr Val Val Thr Asp His Gly
            930                 935                 940

Ser Cys Val Arg Ala Cys Gly Ala Asp Ser Tyr Glu Met Glu Glu Asp
945                 950                 955                 960

Gly Val Arg Lys Cys Lys Lys Cys Glu Gly Pro Cys Arg Lys Val Cys
                    965                 970                 975

Asn Gly Ile Gly Ile Gly Glu Phe Lys Asp Ser Leu Ser Ile Asn Ala
            980                 985                 990
```

Thr Asn Ile Lys His Phe Lys Asn Cys Thr Ser Ile Ser Gly Asp Leu
            995                 1000                1005

His Ile Leu Pro Val Ala Phe Arg Gly Asp Ser Phe Thr His Thr
    1010                1015                1020

Pro Pro Leu Asp Pro Gln Glu Leu Asp Ile Leu Lys Thr Val Lys
    1025                1030                1035

Glu Ile Thr Gly Phe Leu Leu Ile Gln Ala Trp Pro Glu Asn Arg
    1040                1045                1050

Thr Asp Leu His Ala Phe Glu Asn Leu Glu Ile Ile Arg Gly Arg
    1055                1060                1065

Thr Lys Gln His Gly Gln Phe Ser Leu Ala Val Val Ser Leu Asn
    1070                1075                1080

Ile Thr Ser Leu Gly Leu Arg Ser Leu Lys Glu Ile Ser Asp Gly
    1085                1090                1095

Asp Val Ile Ile Ser Gly Asn Lys Asn Leu Cys Tyr Ala Asn Thr
    1100                1105                1110

Ile Asn Trp Lys Lys Leu Phe Gly Thr Ser Gly Gln Lys Thr Lys
    1115                1120                1125

Ile Ile Ser Asn Arg Gly Glu Asn Ser Cys Lys Ala Thr Gly Gln
    1130                1135                1140

Val Cys His Ala Leu Cys Ser Pro Glu Gly Cys Trp Gly Pro Glu
    1145                1150                1155

Pro Arg Asp Cys Val Ser Cys Arg Asn Val Ser Arg Gly Arg Glu
    1160                1165                1170

Cys Val Asp Lys Cys Asn Leu Leu Glu Gly Glu Pro Arg Glu Phe
    1175                1180                1185

Val Glu Asn Ser Glu Cys Ile Gln Cys His Pro Glu Cys Leu Pro
    1190                1195                1200

Gln Ala Met Asn Ile Thr Cys Thr Gly Arg Gly Pro Asp Asn Cys
    1205                1210                1215

Ile Gln Cys Ala His Tyr Ile Asp Gly Pro His Cys Val Lys Thr
    1220                1225                1230

Cys Pro Ala Gly Val Met Gly Glu Asn Asn Thr Leu Val Trp Lys
    1235                1240                1245

Tyr Ala Asp Ala Gly His Val Cys His Leu Cys His Pro Asn Cys
    1250                1255                1260

Thr Tyr Gly Cys Thr Gly Pro Gly Leu Glu Gly Cys Pro Thr Asn
    1265                1270                1275

Gly Pro Lys Ile Pro Ser Ile Ala Thr Gly Met Val Gly Ala Leu
    1280                1285                1290

Leu Leu Leu Leu Val Val Ala Leu Gly Ile Gly Leu Phe Met
    1295                1300                1305

<210> SEQ ID NO 21
<211> LENGTH: 86
<212> TYPE: PRT
<213> ORGANISM: Artificial sequence
<220> FEATURE:
<223> OTHER INFORMATION: intracellular 4-1BB_4-1BB domain (human)

<400> SEQUENCE: 21

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

-continued

```
Pro Glu Glu Glu Gly Gly Cys Glu Leu Ser Thr Lys Arg Gly Arg
         35                  40                  45

Lys Lys Leu Leu Tyr Ile Phe Lys Gln Pro Phe Met Arg Pro Val Gln
 50                  55                  60

Thr Thr Gln Glu Glu Asp Gly Cys Ser Cys Arg Phe Pro Glu Glu Glu
 65                  70                  75                  80

Glu Gly Gly Cys Glu Leu
             85

<210> SEQ ID NO 22
<211> LENGTH: 764
<212> TYPE: PRT
<213> ORGANISM: Artificial sequence
<220> FEATURE:
<223> OTHER INFORMATION: anti-LLE CAR CD8Leader-anti-BioVL/VH-IgG4Hinge-
      CD8TM-41BB-CD3

<400> SEQUENCE: 22

Met Ala Leu Pro Val Thr Ala Leu Leu Leu Pro Leu Ala Leu Leu Leu
 1               5                  10                  15

His Ala Ala Arg Pro Asp Val Val Met Thr Gln Thr Pro Leu Ser Leu
                 20                  25                  30

Pro Val Ser Leu Gly Asp Gln Ala Ser Ile Ser Cys Arg Ser Ser Gln
             35                  40                  45

Ser Leu Val His Ser Asn Gly Asn Thr Tyr Leu His Trp Phe Leu Gln
 50                  55                  60

Lys Pro Gly Gln Ser Pro Asn Leu Leu Ile Tyr Lys Val Ser Asn Arg
 65                  70                  75                  80

Phe Ser Gly Val Pro Asp Arg Phe Ser Gly Ser Gly Ser Gly Thr Asp
                 85                  90                  95

Phe Thr Leu Lys Ile Ser Arg Val Glu Ala Glu Asp Leu Gly Val Tyr
             100                 105                 110

Phe Cys Ser Gln Ser Thr His Val Pro Tyr Thr Phe Gly Gly Gly Thr
             115                 120                 125

Lys Leu Glu Ile Lys Gly Gly Gly Gly Ser Gly Gly Gly Ser Gly
         130                 135                 140

Gly Gly Gly Ser Glu Val Gln Leu Val Glu Ser Gly Gly Gly Leu Val
145                 150                 155                 160

Lys Pro Gly Gly Ser Leu Lys Leu Ser Cys Ala Val Ser Gly Phe Thr
                 165                 170                 175

Phe Ser Asn Tyr Ala Met Ser Trp Val Arg Gln Thr Pro Glu Thr Arg
             180                 185                 190

Leu Asn Trp Val Ala Thr Ile Thr Gly Gly Gly Ser Tyr Thr Tyr Tyr
         195                 200                 205

Pro Asp Ser Val Lys Gly Arg Phe Thr Ile Ser Arg Asp Asn Ala Lys
     210                 215                 220

Asp Thr Leu Tyr Leu Gln Met Ser Ser Leu Arg Ser Glu Asp Thr Ala
225                 230                 235                 240

Met Tyr Tyr Cys Val Arg Gln Arg Val Gly Asp Tyr Val Ser Ser Leu
                 245                 250                 255

Leu Gly Tyr Trp Gly Gln Gly Thr Leu Val Thr Val Ser Ala Ala Ser
             260                 265                 270

Glu Ser Lys Tyr Gly Pro Pro Cys Pro Pro Cys Pro Ile Tyr Ile Trp
         275                 280                 285

Ala Pro Leu Ala Gly Thr Cys Gly Val Leu Leu Leu Ser Leu Val Ile
     290                 295                 300
```

```
Thr Leu Tyr Cys Lys Arg Gly Arg Lys Lys Leu Leu Tyr Ile Phe Lys
305                 310                 315                 320
Gln Pro Phe Met Arg Pro Val Gln Thr Thr Gln Glu Glu Asp Gly Cys
            325                 330                 335
Ser Cys Arg Phe Pro Glu Glu Glu Gly Cys Glu Leu Arg Val
            340                 345                 350
Lys Phe Ser Arg Ser Ala Asp Ala Pro Ala Tyr Gln Gln Gly Gln Asn
            355                 360                 365
Gln Leu Tyr Asn Glu Leu Asn Leu Gly Arg Arg Glu Glu Tyr Asp Val
            370                 375                 380
Leu Asp Lys Arg Arg Gly Arg Asp Pro Glu Met Gly Gly Lys Pro Arg
385                 390                 395                 400
Arg Lys Asn Pro Gln Glu Gly Leu Tyr Asn Glu Leu Gln Lys Asp Lys
            405                 410                 415
Met Ala Glu Ala Tyr Ser Glu Ile Gly Met Lys Gly Glu Arg Arg Arg
            420                 425                 430
Gly Lys Gly His Asp Gly Leu Tyr Gln Gly Leu Ser Thr Ala Thr Lys
            435                 440                 445
Asp Thr Tyr Asp Ala Leu His Met Gln Ala Leu Pro Pro Arg Arg Ala
            450                 455                 460
Lys Arg Ser Ala Gly Ser Gly Ala Thr Asn Phe Ser Leu Leu Lys Gln
465                 470                 475                 480
Ala Gly Asp Val Glu Glu Asn Pro Gly Pro Met Gly Ala Gly Ala Thr
            485                 490                 495
Gly Arg Ala Met Asp Gly Pro Arg Leu Leu Leu Leu Leu Leu Leu Gly
            500                 505                 510
Val Ser Leu Gly Gly Ala Lys Glu Ala Cys Pro Thr Gly Leu Tyr Thr
            515                 520                 525
His Ser Gly Glu Cys Cys Lys Ala Cys Asn Leu Gly Glu Gly Val Ala
            530                 535                 540
Gln Pro Cys Gly Ala Asn Gln Thr Val Cys Glu Pro Cys Leu Asp Ser
545                 550                 555                 560
Val Thr Phe Ser Asp Val Val Ser Ala Thr Glu Pro Cys Lys Pro Cys
            565                 570                 575
Thr Glu Cys Val Gly Leu Gln Ser Met Ser Ala Pro Cys Val Glu Ala
            580                 585                 590
Asp Asp Ala Val Cys Arg Cys Ala Tyr Gly Tyr Tyr Gln Asp Glu Thr
            595                 600                 605
Thr Gly Arg Cys Glu Ala Cys Arg Val Cys Glu Ala Gly Ser Gly Leu
            610                 615                 620
Val Phe Ser Cys Gln Asp Lys Gln Asn Thr Val Cys Glu Glu Cys Pro
625                 630                 635                 640
Asp Gly Thr Tyr Ser Asp Glu Ala Asn His Val Asp Pro Cys Leu Pro
            645                 650                 655
Cys Thr Val Cys Glu Asp Thr Glu Arg Gln Leu Arg Glu Cys Thr Arg
            660                 665                 670
Trp Ala Asp Ala Glu Cys Glu Glu Ile Pro Gly Arg Trp Ile Thr Arg
            675                 680                 685
Ser Thr Pro Pro Glu Gly Ser Asp Ser Thr Ala Pro Ser Thr Gln Glu
            690                 695                 700
Pro Glu Ala Pro Pro Glu Gln Asp Leu Ile Ala Ser Thr Val Ala Gly
705                 710                 715                 720
```

-continued

```
Val Val Thr Thr Val Met Gly Ser Ser Gln Pro Val Thr Arg Gly
            725                 730                 735

Thr Thr Asp Asn Leu Ile Pro Val Tyr Cys Ser Ile Leu Ala Ala Val
        740                 745                 750

Val Val Gly Leu Val Ala Tyr Ile Ala Phe Lys Arg
        755                 760

<210> SEQ ID NO 23
<211> LENGTH: 797
<212> TYPE: PRT
<213> ORGANISM: Artificial sequence
<220> FEATURE:
<223> OTHER INFORMATION: anti-LLE CAR CD8Leader-anti-BioVL/VH-CD8stalk-
      CD8TM-41BB-CD3

<400> SEQUENCE: 23

Met Ala Leu Pro Val Thr Ala Leu Leu Leu Pro Leu Ala Leu Leu Leu
1               5                   10                  15

His Ala Ala Arg Pro Asp Val Val Met Thr Gln Thr Pro Leu Ser Leu
            20                  25                  30

Pro Val Ser Leu Gly Asp Gln Ala Ser Ile Ser Cys Arg Ser Ser Gln
        35                  40                  45

Ser Leu Val His Ser Asn Gly Asn Thr Tyr Leu His Trp Phe Leu Gln
    50                  55                  60

Lys Pro Gly Gln Ser Pro Asn Leu Leu Ile Tyr Lys Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Leu Gly Val Tyr
            100                 105                 110

Phe Cys Ser Gln Ser Thr His Val Pro Tyr Thr Phe Gly Gly Gly Thr
        115                 120                 125

Lys Leu Glu Ile Lys Gly Gly Gly Gly Ser Gly Gly Gly Ser Gly
    130                 135                 140

Gly Gly Gly Ser Glu Val Gln Leu Val Glu Ser Gly Gly Gly Leu Val
145                 150                 155                 160

Lys Pro Gly Gly Ser Leu Lys Leu Ser Cys Ala Val Ser Gly Phe Thr
                165                 170                 175

Phe Ser Asn Tyr Ala Met Ser Trp Val Arg Gln Thr Pro Glu Thr Arg
            180                 185                 190

Leu Asn Trp Val Ala Thr Ile Thr Gly Gly Gly Ser Tyr Thr Tyr Tyr
        195                 200                 205

Pro Asp Ser Val Lys Gly Arg Phe Thr Ile Ser Arg Asp Asn Ala Lys
    210                 215                 220

Asp Thr Leu Tyr Leu Gln Met Ser Ser Leu Arg Ser Glu Asp Thr Ala
225                 230                 235                 240

Met Tyr Tyr Cys Val Arg Gln Arg Val Gly Asp Tyr Val Ser Ser Leu
                245                 250                 255

Leu Gly Tyr Trp Gly Gln Gly Thr Leu Val Thr Val Ser Ala Ala Ser
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320
```

```
Trp Ala Pro Leu Ala Gly Thr Cys Gly Val Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
                355                 360                 365

Cys Ser Cys Arg Phe Pro Glu Glu Glu Glu Gly Gly Cys Glu Leu Arg
        370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
                435                 440                 445

Lys Met Ala Glu Ala Tyr Ser Glu Ile Gly Met Lys Gly Glu Arg Arg
        450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg Arg
                485                 490                 495

Ala Lys Arg Ser Ala Gly Ser Gly Ala Thr Asn Phe Ser Leu Leu Lys
            500                 505                 510

Gln Ala Gly Asp Val Glu Glu Asn Pro Gly Pro Met Gly Ala Gly Ala
                515                 520                 525

Thr Gly Arg Ala Met Asp Gly Pro Arg Leu Leu Leu Leu Leu Leu Leu
        530                 535                 540

Gly Val Ser Leu Gly Gly Ala Lys Glu Ala Cys Pro Thr Gly Leu Tyr
545                 550                 555                 560

Thr His Ser Gly Glu Cys Cys Lys Ala Cys Asn Leu Gly Glu Gly Val
                565                 570                 575

Ala Gln Pro Cys Gly Ala Asn Gln Thr Val Cys Glu Pro Cys Leu Asp
            580                 585                 590

Ser Val Thr Phe Ser Asp Val Val Ser Ala Thr Glu Pro Cys Lys Pro
                595                 600                 605

Cys Thr Glu Cys Val Gly Leu Gln Ser Met Ser Ala Pro Cys Val Glu
        610                 615                 620

Ala Asp Asp Ala Val Cys Arg Cys Ala Tyr Gly Tyr Tyr Gln Asp Glu
625                 630                 635                 640

Thr Thr Gly Arg Cys Glu Ala Cys Arg Val Cys Glu Ala Gly Ser Gly
                645                 650                 655

Leu Val Phe Ser Cys Gln Asp Lys Gln Asn Thr Val Cys Glu Glu Cys
            660                 665                 670

Pro Asp Gly Thr Tyr Ser Asp Glu Ala Asn His Val Asp Pro Cys Leu
                675                 680                 685

Pro Cys Thr Val Cys Glu Asp Thr Glu Arg Gln Leu Arg Glu Cys Thr
        690                 695                 700

Arg Trp Ala Asp Ala Glu Cys Glu Glu Ile Pro Gly Arg Trp Ile Thr
705                 710                 715                 720

Arg Ser Thr Pro Pro Glu Gly Ser Asp Ser Thr Ala Pro Ser Thr Gln
                725                 730                 735
```

-continued

```
Glu Pro Glu Ala Pro Pro Glu Gln Asp Leu Ile Ala Ser Thr Val Ala
            740                 745                 750

Gly Val Val Thr Thr Val Met Gly Ser Ser Gln Pro Val Val Thr Arg
        755                 760                 765

Gly Thr Thr Asp Asn Leu Ile Pro Val Tyr Cys Ser Ile Leu Ala Ala
        770                 775                 780

Val Val Val Gly Leu Val Ala Tyr Ile Ala Phe Lys Arg
785                 790                 795
```